United States Patent
Moseley et al.

(10) Patent No.: US 10,607,723 B2
(45) Date of Patent: Mar. 31, 2020

(54) METHOD AND SYSTEM FOR IDENTIFICATION OF METABOLITES USING MASS SPECTRA

(71) Applicant: UNIVERSITY OF KENTUCKY RESEARCH FOUNDATION, Lexington, KY (US)

(72) Inventors: Hunter N. B. Moseley, Lexington, KY (US); William J. Carreer, Lexington, KY (US); Joshua Mitchell, Lexington, KY (US); Robert M. Flight, Lexington, KY (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 297 days.

(21) Appl. No.: 15/642,143

(22) Filed: Jul. 5, 2017

(65) Prior Publication Data

US 2018/0011990 A1    Jan. 11, 2018

Related U.S. Application Data

(60) Provisional application No. 62/358,411, filed on Jul. 5, 2016.

(51) Int. Cl.
*G01N 33/50* (2006.01)
*G01N 33/68* (2006.01)
(Continued)

(52) U.S. Cl.
CPC .............. *G16C 20/20* (2019.02); *A61B 5/055* (2013.01); *G01N 33/5038* (2013.01);
(Continued)

(58) Field of Classification Search
CPC ......... G06F 19/00; G06F 19/10; A61B 5/055; G01N 33/50; G01N 33/68; H01J 49/26
(Continued)

(56) References Cited

U.S. PATENT DOCUMENTS

| 6,764,817 B1 | 7/2004 | Schneider |
|---|---|---|
| 7,402,437 B2 | 7/2008 | Gonzalez et al. |

(Continued)

FOREIGN PATENT DOCUMENTS

| JP | 2008/151856 | 12/2006 |
|---|---|---|
| WO | WO-2013/170099 A1 | 11/2013 |

OTHER PUBLICATIONS

Hellerstein, M. K. et al, American Journal of Physiology 1999, 276, E1146-E1170.*

(Continued)

*Primary Examiner* — Arlen Soderquist
(74) *Attorney, Agent, or Firm* — Stephen J. Weyer, Esq.; Mandy Wilson Decker, Esq.; Stites & Harbison, PLLC

(57) ABSTRACT

A method and system is provided for mass spectrometry for identification of a specific elemental formula for an unknown compound which includes but is not limited to a metabolite. The method includes calculating a natural abundance probability (NAP) of a given isotopologue for isotopes of non-labelling elements of an unknown compound. Molecular fragments for a subset of isotopes identified using the NAP are created and sorted into a requisite cache data structure to be subsequently searched. Peaks from raw spectrum data from mass spectrometry for an unknown compound. Sample-specific peaks of the unknown compound from various spectral artifacts in ultra-high resolution Fourier transform mass spectra are separated. A set of possible isotope-resolved molecular formula (IMF) are created by iteratively searching the molecular fragment caches
(Continued)

and combining with additional isotopes and then statistically filtering the results based on NAP and mass-to-charge (m/2) matching probabilities. An unknown compound is identified and its corresponding elemental molecular formula (EMF) from statistically-significant caches of isotopologues with compatible IMFs.

17 Claims, 19 Drawing Sheets

(51) Int. Cl.
*A61B 5/055* (2006.01)
*H01J 49/26* (2006.01)
*G16C 20/20* (2019.01)
*G01R 33/46* (2006.01)
*G01R 33/465* (2006.01)
*H01J 49/00* (2006.01)
*G16B 40/10* (2019.01)
*G16B 99/00* (2019.01)
*G01N 24/08* (2006.01)

(52) U.S. Cl.
CPC ....... *G01N 33/6848* (2013.01); *G01R 33/465* (2013.01); *G01R 33/4633* (2013.01); *G16B 40/10* (2019.02); *H01J 49/0036* (2013.01); *G01N 24/08* (2013.01); *G16B 99/00* (2019.02); *H01J 49/26* (2013.01)

(58) Field of Classification Search
USPC .................. 436/86, 91–99, 127–132, 173; 702/22–23, 27
See application file for complete search history.

(56) References Cited

U.S. PATENT DOCUMENTS

| | | | |
|---|---|---|---|
| 8,116,983 B2 | 2/2012 | Ramsay et al. | |
| 8,129,335 B2 | 3/2012 | Hellerstein | |
| 8,420,406 B2 | 4/2013 | Lüdemann et al. | |
| 8,481,478 B2 | 7/2013 | Hellerstein | |
| 8,510,054 B2 | 8/2013 | Iwatani et al. | |
| 2003/0078739 A1* | 4/2003 | Norton | G06K 9/00523 702/22 |
| 2003/0108876 A1* | 6/2003 | Speir | G01N 33/5008 435/6.12 |
| 2003/0180710 A1 | 9/2003 | Lee et al. | |
| 2003/0180800 A1 | 9/2003 | Lee et al. | |
| 2005/0107957 A1* | 5/2005 | Heath | G06T 11/206 702/19 |
| 2005/0175982 A1 | 8/2005 | Itwatani et al. | |
| 2005/0181455 A1* | 8/2005 | Alberte | C07O 305/24 435/7.1 |
| 2005/0281745 A1 | 12/2005 | Lee et al. | |
| 2006/0085141 A1* | 4/2006 | Neacsu | H01J 49/0036 702/23 |
| 2006/0094057 A1 | 5/2006 | Hellerstein | |
| 2006/0288339 A1* | 12/2006 | Wang | G16C 20/20 717/155 |
| 2007/0114373 A1* | 5/2007 | Zweigenbaum | H01J 49/0036 250/282 |
| 2007/0141712 A1* | 6/2007 | Ludemann | G01N 33/58 436/57 |
| 2008/0052011 A1* | 2/2008 | Wang | H01J 49/0036 702/27 |
| 2008/0081375 A1 | 4/2008 | Tesiram | |
| 2008/0140370 A1* | 6/2008 | Kuhlmann | G16C 20/20 703/11 |
| 2009/0076737 A1* | 3/2009 | Wang | G01N 33/6848 702/23 |
| 2009/0299653 A1* | 12/2009 | Pfaff | G06K 9/00543 702/28 |
| 2009/0302213 A1* | 12/2009 | Kuehl | H01J 49/0009 250/282 |
| 2012/0108448 A1* | 5/2012 | Kuhlmann | H01J 49/0036 506/8 |
| 2013/0041592 A1* | 2/2013 | York | G01N 33/5308 702/19 |
| 2014/0045273 A1* | 2/2014 | Cerda | G01N 27/62 436/173 |
| 2014/0212872 A1 | 7/2014 | Milburn et al. | |
| 2014/0316718 A1* | 10/2014 | Crowell | H01J 49/0036 702/32 |
| 2014/0379279 A1* | 12/2014 | Pfaff | G06K 9/00543 702/28 |
| 2015/0228464 A1* | 8/2015 | Duchoslav | H01J 49/004 250/282 |
| 2015/0340216 A1* | 11/2015 | Kwiecien | G06K 9/00543 250/282 |

OTHER PUBLICATIONS

Aharoni, A. et a, Omics 2002, 6, 217-234.*
Wahl, S. A. et al, Biotechnology and Bioengineering 2004, 85, 259-268.*
Kujawinski, E. B. et al, Analytical Chemistry 2006, 78, 4363-4373.*
Stoll, N. et al, Journal of the American Society for Mass Spectrometry 2006, 17, 1692-1699.*
Hobby, K. et al, Rapid Communications in Mass spectrometry 2009, 23, 219-227.*
Rogers, S. et al, Bioinformatics 2009, 25, 512-518.*
Payne, T. G. et al, Journal of the American Society for Mass Spectrometry 2009, 20, 1087-1095.*
Feldberg, L. et al, Analytical Chemistry 2009, 81, 9257-9266.*
Kunenkov, E. V. et al, Analytical Chemistry 2009, 81, 10106-10115.*
Ohta, D. et al, Current Opinion in Biotechnology 2010, 21, 35-44.*
Weber, R. J. M. et al, Chemometrics and Intelligent Laboratory Systems 2010, 104, 75-82.*
Miura, D. et al, Analytical Chemistry 2010, 82, 5887-5891.*
Meringer, M. et al, MATCH—Communications in Mathematical and in Computer Chemistry 2011, 65, 259-290.*
Brown, M. et al, Bioinformatics 2011, 27, 1108-1112.*
Kueger, S. et al, The Plant Journal 2012, 70, 39-50.*
Pluskal, T. et al, Analytical Chemistry 2012, 84, 4396-4403.*
Allwood, J. W. et al, in "Plant Metabolomics: Methods and Protocols, Methods in Molecular Biology" Hardy, N. W. et al, Ed., Springer Science+Business Media, 2012, 860, 157-176.*
Millard, P. et al, Bioinformatics 2012, 28, 1294-1296.*
Marti, R. et al, European Journal of Operational Research 2013, 226, 1-8.*
Chokkathukalam, A. et al, Bioinformatics 2013, 29, 281-283.*
Sakurai, N. et al, Bioinformatics 2013, 29, 290-291.*
Carreer, W. J. et al, Metabolites 2013, 3, 853-866.*
Pollier, J. et al, in "Jasnnonate Signaling: Methods and Protocols, Methods in Molecular Biology" Goossens, A. et al, Ed., Springer Science+Business Media, 2013, 1011, 227-286.*
Chiron, L. et al, Proceedings of the National Academy of Sciences of the United States of America 2014, 111, 1385-1390.*
Ipsen, A, Analytical Chemistry 2014, 86, 5316-5322.*
Daly, R. et al, Bioinformatics 2014, 30, 2764-2771.*
Mitchell, J. M. et al, Frontiers in Genetics 2014, 5, Article 237, 18 pages.*
Loos, M. et al, Analytical Chemistry 2015, 87, 5738-5744.*
Niedenfuhr, S. et al, Biotechnology and Bioengineering 2016, 113, 1137-1147.*
Mitchell, J. M. et al, Metabolomics 2018, 14, paper 125, 11 pages.*
Mitchell, J. M. et al, Analytical Chemistry 2019, 91, 8933-8940.*
Hastings, C. A. et al, Rapid Communications in Mass Spectrometry 2002, 16, 462-467.*
Kast, J. et al, Journal of the American Society for Mass Spectrometry 2003, 14, 766-776.*
Prost, S. A. et al, Journal of the American Society for Mass Spectrometry 2014, 25, 2020-2027.*

(56) References Cited

OTHER PUBLICATIONS

Moseley, H., Correcting for the effects of natural abundance in stable isotope resolved metabolomics experiments involving ultra-high resolution mass spectrometry. BMC Bioinformatics, 2010. 11: p. 139.
Lane, A.N., T.W. Fan, Z. Xie, H.N. Moseley, and R.M. Higashi, Isotopomer analysis of lipid biosynthesis by high resolution mass spectrometry and NMR. Analytica Chimica Acta, 2009. 651(2): p. 201-8.
Fan, T.W. and A.N. Lane, NMR-based stable isotope resolved metabolomics in systems biochemistry. Journal of Biomolecular NMR, 2017. 49(3-4): p. 267-80.
Lane, A.N., T.W. Fan, and R.M. Higashi, Isotopomer-based metabolomic analysis by NMR and mass spectrometry. Methods Cell Biol, 2008. 84: p. 541-88.
Moseley, H., A. Lane, A. Belshoff, R. Higashi, and T. Fan, A novel deconvolution method for modeling UDP-GlcNAc biosynthetic pathways based on 13C mass isotopologue profiles under non steady-state conditions. BMC Biology, 2011. 9(1): p. 37.
Tomita, E., A. Tanaka, and H. Takahashi, The worst-case time complexity for generating all maximal cliques and computational experiments. Theoretical Computer Science, 2006. 363(1): p. 28-42.
Cazals, F. and C. Karande, A note on the problem of reporting maximal cliques. Theoretical Computer Science, 2008. 407(1-3): p. 564-568.
Eppstein, D., M. LOffler, and D. Strash, Listing all maximal cliques in sparse graphs in near-optimal time. Algorithms and Computation, 2010: p. 403-414.
Lorkiewicz, P.K., R.M. Higashi, A.N. Lane, and T.W.-M. Fan, High information throughput analysis of nucleotides and their isotopically enriched isotopologues by direct-infusion FTICR-MS. Metabolomics, 2012. in press.
Fan, T., M. Kucia, K. Jankowski, R. Higashi, J. Ratajczak, M. Ratajczak, and A. Lane, Rhabdomyosarcoma cells show an energy producing anabolic metabolic phenotype compared with primary myocytes. Molecular Cancer, 2008. 7(1): p. 79.
Lane, A.N., T.W. Fan, and R.M. Higashi, Stable isotope-assisted metabolomics in cancer research. IUBMB Life, 2008. 60(2): p. 124-9.
Fan, T.W.M., P. Lorkiewicz, K Sellers, H.N.B. Moseley, R.M. Higashi, and A.N. Lane, Stable isotope-resolved metabolomics and applications for drug development. Pharmacology & Therapeutics, 2012. 133(3): p. 366-391.
Cui, Q., I.A. Lewis, A.D. Hegeman, M.E. Anderson, J. Li, C.F. Schulte, W.M. Westler, H.R. Eghbalnia, M.R. Sussman, and J.L. Markley, Metabolite identification via the Madison Metabolomics Consortium Database. Nature Biotechnology, 2008. 26(2): p. 162-164.
Wishart, D., D. Tzur, C. Knox, R. Eisner, A. Guo, N. Young, D. Cheng, K. Jewell, D. Arndt, and S. Sawhney, HMDB: the human metabolome database. Nucleic Acids Research, 2007. 35(Database issue): p. D521.
Kanehisa, M., S. Goto, M. Hattori, K. Aoki-Kinoshita, M. Itoh, S. Kawashima, T. Katayama, M. Araki, and M. Hirakawa, From genomics to chemical genomics: new developments in KEGG. Nucleic Acids Research, 2006. 34(Database Issue): p. D354.
Redestig, H., M. Kusano, A. Fukushima, F. Matsuda, K Saito, and M. Arita, Consolidating metabolite identifiers to enable contextual and multi-platform metabolomics data analysis. BMC bioinformatics, 2010. 11(1): p. 214.
Pence, H.E and A. Williams, ChemSpider: an online chemical information resource. Journal of Chemical Education, 2010.
Kanehisa, et al., KEGG: Kyoto Encyclopedia of Genes and Genomes. Nucleic Acids Res, 1999. 27(1): p. 29-34.
Bonacich, P., Factoring and weighting approaches to status scores and clique identification. Journal of Mathematical Sociology, 1972. 2(1): p. 113-120.
Kose, F., W. Weckwerth, T. Linke, and 0. Fiehn, Visualizing plant metabolomic correlation networks using clique-metabolite matrices. Bioinformatics, 2001. 17(12): p. 1198-1208.

Benjamini, Y. and Y. Hochberg, Controlling the false discovery rate: A practical and powerful approach to multiple testing. . J. Roy. Statist. Soc. B, 1995. 57: p. 289-300.
Taylor, R.P., G.J. Parker, Mm. Hazel, Y. Soesanto, W. Fuller, M J Yazzie, and D.A. McClain, Glucose deprivation stimulates O-GlcNAc modification of proteins through up-regulation of 0-linked N-acetylglucosaminyltransferase. J Biol Chem, 2008. 283(10): p. 6050-7.
Wahl, S.A., K. MTh, and W. Wiechert, 13C labeling experiments at metabolic nonstationary conditions: an exploratory study. BMC bioinformatics, 2008. 9(1): p. 152.
Selivanov, V.A., S. Marin, P.W.N. Lee, and M. Cascante, Software for dynamic analysis of tracer-based metabolomic data: estimation of metabolic fluxes and their statistical analysis. Bioinformatics, 2006. 22(22): p. 2806-2812.
Arita, M., In silico atomic tracing by substrate-product relationships in *Escherichia coli* intermediary metabolism. Genome Research, 2003. 13(11): p. 2455-2466.
Caspi, R., H. Foerster, C.A. Fulcher, P. Kaipa, M. Krummenacker, M. Latendresse, S. Paley, S.Y. Rhee, A.G. Shearer, and C. Tissier, The MetaCyc database of metabolic pathways and enzymes and the BioCyc collection of pathway/genome databases. Nucleic acids research, 2008. 36(suppl 1): p. D623-D631.
Krieger, C.J., P. Zhang, L.A. Mueller, A. Wang, S. Paley, M. Arnaud, J. Pick, S.Y. Rhee, and P.D. Karp, MetaCyc: a multiorganism database of metabolic pathways and enzymes. Nucleic acids research, 2004. 32(suppl 1): p. D438-D442.
Eppstein, D., Finding the k shortest paths. SIAM J. Comput., 1998. 28(2): p. 652-673.
Hershberger, J., M. Maxel, and S. Suri, Finding the k shortest simple paths: A new algorithm and its implementation. ACM Transactions on Algorithms (TALG), 2007. 3(4): p. 45.
Akaike, H., A new look at the statistical model identification. IEEE transactions on automatic control, 1974. 19(6): p. 716-723.
Fan, T., L. Bandura, R. Higashi, and A. Lane, Metabolomics-edited transcriptomics analysis of Se anticancer action in human lung cancer cells. Metabolomics Journal, 2005. 1(4): p. 325-339.
Birkemeyer, et al. Metabolome analysis: the potential of in vivo labeling with stable isotopes for metabolite profiling Trends in Biotechnology, 2005, 23(1): 29-33.
Browne, et al. Performance of human mass balance/metabolite identification studies using stable isotope (13C, 15N) labeling and continuous-flow isotope-ratio mass spectrometry as an alternative to radioactive labeling methods. J Clin Pharmacol. Mar. 1993;33(3):246-52.
Creek, et al. Stable Isotope-Assisted Metabolomics for Network-Wide Metabolic Pathway Elucidation Analytical Chemistry 2012, 84, 8442-8447.
Dunn, et al. Mass appeal: metabolite identification in mass spectrometry-focused untargeted metabolomics Metabolomics, 2013, 9, S44-S66.
Kumari, et al. Applying in-silico retention index and mass spectra matching for identification of unknown metabolites in accurate mass GC-TOF mass spectrometry. Anal Chem. Aug. 1, 2011;83(15):5895-902.
Nakayama, et al. Novel Strategy for Non-Targeted Isotope-Assisted Metabolomics by Means of Metabolic Turnover and Multivariate AnalysisMetabolites, 2014; 4: 722-739.
Sano, et al. A new technique for the detection of metabolites labelled by the isotope 13C using mass fragmentography. Biomed Mass Spectrom. Feb. 1976; 3(1): 1-3.
VandenHeuvel, WJ. Drug metabolite identification: stable isotope methods. J Clin Pharmacol. Jul.-Aug. 1986;26(6):427-34.
Yan, et al., Rapid detection and characterization of minor reactive metabolites using stable-isotope trapping in combination with tandem mass spectrometry. Rapid Commun Mass Spectrom. 2005;19(22):3322-30.
Yang, et al. In vitro stable isotope labeling for discovery of novel metabolites by liquid chromatography-mass spectrometry: Confirmation of gamma-tocopherol metabolism in human A549 cell. J Chromatogr A. Jan. 29, 2010;1217(5):667-75. doi: 10.1016/j.chroma.2009.12.002. Epub Dec. 4, 2009.
Yang, et al. Simultaneous quantification of metabolites involved in central carbon and energy metabolism using reversed-phase liquid

(56) References Cited

OTHER PUBLICATIONS chromatography-mass spectrometry and in vitro 13C labeling. Anal Chem. Dec. 15, 2008;80(24):9508-16.

You, et al. Application of Stable Isotope-Assisted Metabolomics for Cell Metabolism StudiesMetabolites, 2014, 4: 142-165.

Richard Baran, Benjamin P. Bowen, Nicholas J. Bouskill, Eoin L. Brodie, Steven M. Yannone, and Trent R. Northen; Metabolite Identification in *Synechococcus* sp. PCC 7002 Using Untargeted Stable Isotope Assisted Metabolite Profiling; Analytical Chemistry 2010 82 (21), 9034-9042.

Nora K. N. Neumann†, Sylvia M. Lehner, Bernhard Kluger, Christoph Bueschl, Karoline Sedelmaiert, Marc Lemmens, Rudolf Krska, and Rainer Schuhmacher; Automated LC-HRMS(/MS) Approach for the Annotation of Fragment Ions Derived from Stable Isotope Labeling-Assisted Untargeted Metabolomics; Anal. Chem., 2014, 86 (15), pp. 7320-7327.

Bowen, et al., Dealing with the Unknown: Metabolomics and Metabolite Atlases; Benjamin P. Bowen and Trent R. Northen; Journal of the American Society for Mass Spectrometry; vol. 21, Issue 9, Sep. 2010, pp. 1471-1476.

MetaSIRM$^{TM}$ Stable Isotope Ratio Metabolomics; http://www.targetdiscovery.com; 20Brief_RevA, pp. 1-9, 2004.

Kind, et al., Metabolomic database annotations via query of elemental compositions: Mass accuracy is insufficient even at less than 1 ppm, BMC Bioinformatics 2006, 7:234, pp. 1-10.

Darren J Creek; Stable isotope labeled metabolomics improves identification of novel metabolites and pathways; Bioanalysis; Aug. 2013 ,vol. 5, No. 15, pp. 1807-1810.

Baran, Richard, Mapping Microbial Metabolism Using Metabolomics, Berkelye Lab; Mar. 6, 2013 pp. 1-18.

\* cited by examiner

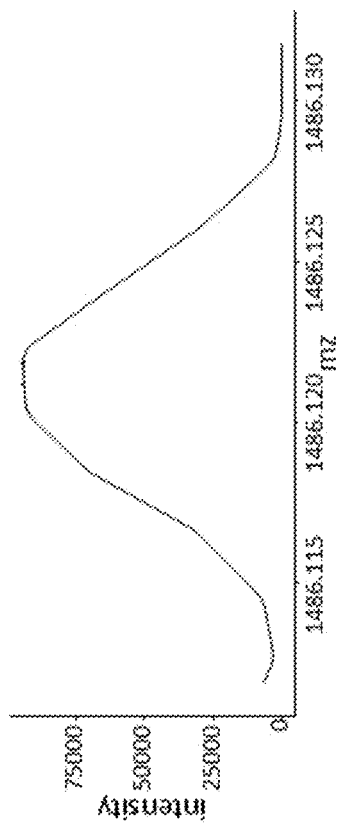
FIG. 4A
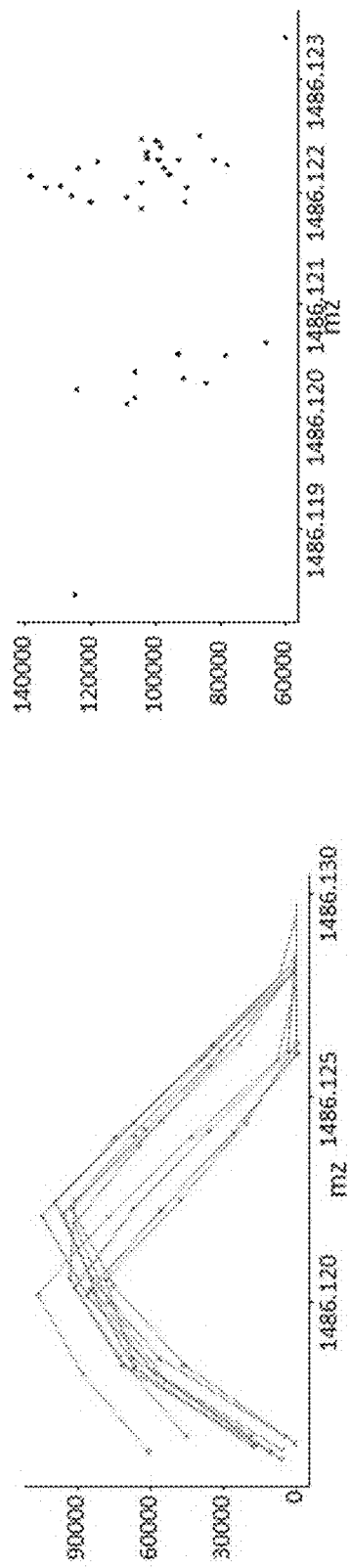
FIG. 4B
FIG. 4C

Ringing

Fuzzy Site $I_0 = g0r0a0u0$
$I_1 = g0r0a0u1$
$I_2 = g0r0a0u2 + g0r0a2u0$
$I_3 = g0r0a0u3 + g0r0a2u1$
$I_4 = g0r0a2u2$
$I_5 = g0r5a0u0 + g0r0a2u3$
$I_6 = g6r0a0u0 + g0r5a0u1$
$I_7 = g6r0a0u1 + g0r5a2u0 + g0r5a0u2$
$I_8 = g6r0a2u0 + g6r0a0u2 + g0r5a2u1 + g0r5a0u3$
$I_9 = g6r0a2u1 + g6r0a0u3 + g0r5a2u2$
$I_{10} = g6r0a2u2 + g0r5a2u3$
$I_{11} = g6r5a0u0 + g6r0a2u3$
$I_{12} = g6r5a0u1$
$I_{13} = g6r5a0u2 + g6r5a2u0$
$I_{14} = g6r5a0u3 + g6r5a2u1$
$I_{15} = g6r5a2u2$
$I_{16} = g6r5a2u3$
$I_{17} = $ NA contribution only.

FIG. 13A

METHOD AND SYSTEM FOR IDENTIFICATION OF METABOLITES USING MASS SPECTRA

CROSS REFERENCE TO RELATED APPLICATION

This application claims benefit of U.S. Provisional Application No. 62/358,411, filed Jul. 5, 2016, which is hereby incorporated by reference.

FIELD OF THE INVENTION

The presently-disclosed subject matter relates to methods and systems for identification of an unknown compound. In particular, the presently-disclosed subject matter relates to identification of an unknown compound, which includes but is not limited to metabolites, detected by mass spectrometry, including ultra-high resolution mass spectrometry. The presently-disclosed subject matter further relates to identification of molecular formulas of detected compounds including metabolites.

BACKGROUND OF THE INVENTION

Metabolomics is a systematic detection and study of the metabolites (small biomolecules <2000 Dalton) present in samples derived from living systems. Recent advances in ultra-high resolution mass spectrometry enables rapid detection of tens of thousands of isotopologues (i.e. mass equivalent sets of isotopomers) representing thousands of metabolites. Yet, the necessity for metabolite identification, quantitative analysis, and interpretation, within the context of relevant metabolic networks, represents key barriers to the use of this avalanche of information-rich, phenotypic metabolomics data. In fact, over 50% of detected metabolites remain unidentified in ultra-high resolution mass spectra and there is low confidence in those metabolites identified without a comparison to standards. With stable isotope-resolved metabolomics (SIRM) experiments, comparison to millions (or billions) of isotopically-different chemical standards is not possible.

SUMMARY OF THE INVENTION

This disclosure describes the development, prototyping, and implementation of a novel algorithm that detects metabolites at a desired statistical confidence and determines their specific elemental molecular formula (EMF) using detected sets (i.e. cliques) of related isotopologue peaks with compatible isotope-resolved molecular formulae (IMFs). The methodology works on both mass spectra derived from non-SIRM experiments, but especially on mass spectra from SIRM experiments that contain metabolites labeled with specific stable isotopes like $^{13}C$, $^{15}N$, and $^{2}H$ from a given labeling source and/or from natural abundance. This approach has none of the limitations of current methods that can only detect known metabolites in a database. Thus this new method enables the full interpretation of untargeted metabolomics studies through the identification of metabolites at the level of structural isomers representing the same EMF.

The approach outlined in this disclosure requires five key components to overcome the inherent IMF combinatorial search problem and then identify statistically significant EMFs from tens of thousands of possible IMFs. The five key components are: i) algorithms that calculate the natural abundance probability (NAP) of a given isotopologue for the set of isotopes it contains or a relative NAP if the labeling isotopes are present; ii) algorithms to efficiently build and sort large (multiterabyte) caches of molecular fragments for a subset of isotopes being searched; iii) algorithms that characterize peaks from a raw spectrum and separate sample-specific peaks from various spectral artefacts seen in ultra-high resolution Fourier transform mass spectra; iv) algorithms that create sets of possible IMFs by iteratively searching the molecular fragment caches and combining with additional isotopes and then statistically filtering the results based on NAP and mass-to-charge (m/z) matching probabilities; and v) an algorithm that identify a metabolite and its corresponding EMF from statistically-significant cliques of isotopologues with compatible IMFs. FIG. 1A (flowchart) and FIG. 1B (system schematic) show an overview of how these five components are used to determine statistically significant EMF cliques.

Again, all five components are necessary to determine IMFs of specific isotopologues and related offset peaks via the identification of their associate EMF clique representing a specific metabolite or a set of metabolites that are structural isomers. Also, this approach is applicable to a directed search of known EMFs by building an isotopically-resolved cache (Component 2) for only these known EMFs. And this approach is applicable to the analysis of tandem mass spectroscopic ($MS_n$) data, where the set of possible IMFs of specific fragment isotopologues are probabilistically intersected with the set of possible IMFs of the parent isotopologue.

Component 1.

$$P_E(k_1, k_2, \ldots, k_m) = \binom{E_{Max}}{k_1, k_2, \ldots, k_m} \prod_{x=1}^{m} NA_{E_{lx}}^{k_x}$$

$$NAP = \prod_{j=1}^{n} P_{Ej}$$

The above equations describe the calculation of the natural abundance probability (NAP) for specific isotopically-resolved molecular formulas. In the case where a specific isotope(s) comes from a labeling source, a relative NAP is calculated where that isotope's contribution to the element's probability ($P_E$) is omitted. For isotope combinations for an element containing 3 or more isotopes, one of which is labeled, a relative NAP can be calculated using the remaining isotopes else the relative NAP is set to one.

Component 2.

The problem of searching for probable isotopically-resolved molecular formulas is a huge combinatorial problem that becomes intractable on even large supercomputers for molecular masses over 500 Daltons. In order to make this problem tractable, you must build a large multiterabyte sorted cache of plausible molecular formula fragments using the NAP from Component 1 and metabolite bonding pattern rules for the elements in the cache. In addition, efficient merge sort algorithms are required to effectively sort a list containing 100's of billions of elements and keep the needed disk space required to build the cache to roughly twice the size of the final sorted cache. The cache reduces the molecular formula search time by a ratio of the time to build the cache (typically >1,000 CPU hours) versus the time it takes to search the cache (i.e. milliseconds or better). An example metabolite bonding pattern rule is the number of hydrogen atoms in a molecular formula is bounded by the number of available valence electrons. Current prototype caches take roughly 3 terabytes of storage; however, future caches would grow with available storage capacities. Efficient utilization of the cache requires an in-memory binary search tree approximately equal to: 16*cache_size/4096 bytes.

Component 3.

Detected peaks within spectra collected from Fourier transform mass spectrometers have a variety of data quality issues including m/z peak shifting (FIGS. 2A and 2B), inconsistency in peak heights and areas (FIG. 3), and the presence of artefactual peaks. These data quality issues arise from: i) limitations in digital resolution (FIG. 4); ii) problems with scan-level consistency (FIG. 5); iii) Fourier transform-based artefacts (FIG. 6), and iv) the presence of contaminants. However, standard peak picking methods that average across scans create huge data quality issues. Therefore, an integrated procedure using a combination of new scan-level peak characterization methods along with artefact peak detection methods are required to derive high quality peak characteristics associated with specific isotopologues. Peak characterization at the scan-level is implemented by removing noise peaks per scan, corresponding peaks across scans, and performing normalization of peak heights/areas across scans. The resulting correspondence peaks are used to derive high quality peak heights and areas (FIGS. 7 and 8) while removing many of the high peak density artefacts present but inconsistent at the scan-level. Separate high peak density analyses and contaminant detection will remove or mark the remaining artefactual peaks. A list of contaminant molecules can be based on expected contaminate molecules from the plastics and solvents used in sample preparation including polymers like polyethylene glycol (PEG) and polymer detergents like triton X-100 or derived from quality control samples directly. A difference matrix generated from this list of expected molecules is compared to the difference matrix generated from the peak list derived from a mass spectrum. Rows between the two matrices with a statistically significant number of differences that match are used to assign expected contaminant peaks and derive offsets present in the spectrum.

Component 4.

Each isotopologue is identified by a peak with a specific mass to charge ratio (m/z ratio) position in the 1D mass spectrum. The peak also has an intensity related to the number of ions physically detected in the mass spectrometer. For each characterized isotopologue peak, a set of possible isotopically-resolved molecular formulas (IMFs) are calculated within a specified accuracy tolerance using Component 2 to build specific isotopically-resolved molecular formulas that are then filtered against: i) the NAP from Component 1; ii) a statistical measure of how well the molecular formula matches the m/z ratio (m/z matching probability); and iii) metabolite bonding pattern rules.

Component 5.

A clique of compatible isotopologue peaks associated with a specific EMF is identified via a nonempty intersection between their sets of possible EMFs identify from their possible IMFs. In addition, each complementary pair of isotopologues (i.e. has equal numbers of labeling isotopes) from a specific EMF clique is statistically evaluated using both m/z matching probabilities from Component 3 and a log ratio of isotopologue intensities statistically compared to the log ratio of each IMF NAP from Component 1 (log-ratio match probability). The isotopologue intensities used in the ratios are derived from associated characterized peaks. Each complementary pair represents a statistically evaluated piece of evidence supporting the existence of the associate EMF clique in the mass spectrum. Specific EMF cliques are identified by statistically evaluating the sum of complementary pair probabilities/likelihoods. Restated, a goodness-of-fit score for a clique is created from the sum of pair probabilities/likelihoods. Statistically significant goodness-of-fit scores are evaluated against randomly generated cliques derived from isotopologues of incompatible cliques at a certain significance level. The resulting analysis identifies EMF cliques of isotopologue peaks associated with one or more structural isomers at a specified level of statistical significance.

Table 1 (below) shows a proof of concept application of implementation of Components 1-5 to a peak list derived from a Thermo Orbitrap Fusion Tribrid FTMS spectrum of a biological sample that had been treated with the ECF ($2Cl-CO_2Et$) chemoselection agent. Twenty-seven out of the 31 verified EMF cliques were detected and assigned by the prototype tool, representing an 87% correctly assigned rate. Peaks from one clique were misassigned, representing a 3.6% false discovery rate (FDR). FIGS. 8, 9A and 9B demonstrate the quality of the fit between observed and theoretical relative isotopologue intensities for a detected EMF clique and across a targeted set of verified cliques. The peak characterization in Component 3 has greatly reduced known FTMS ion suppression effects as illustrated by the slope between normalized NAP values and relative intensities in FIG. 9A. These results clearly show the utility of this approach to derive validated EMFs from FTMS peak lists. The current prototype is able to efficiently search a roughly 4.8 quintillion ($4.8 \times 10^{18}$) IMF space for each peak's m/z, based on molecular masses $\leq$=2000 daltons, but larger IMF spaces are searchable.

TABLE 1

Validated EMFs from Biological Sample Detected Using a Prototype Implementation

| EMF | Assignment | Clique Size |
| --- | --- | --- |
| C10E1H17N1Na1O4 | Assigned | 4 |
| C10E1H17N1Na1O6 | Assigned | 3 |
| C10E1H18N2Na1O5 | Assigned | 4 |
| C10E1H19N1Na1O4 | Assigned | 4 |
| C11E1H19N1Na1O6 | Assigned | 5 |
| C11E1H21N1Na1O4 | Assigned | 5 |
| C11E1H21N3Na1O5 | Assigned | 5 |
| C11E1H23N4O4 | Assigned | 2 |
| C12E1H17N3Na1O6 | Assigned | 2 |
| C12E1H20N3O4 | Assigned | 5 |
| C12E1H21N1Na1O6 | Assigned | 3 |
| C12E1H22N2Na1O6 | Assigned | 2 |
| C13E1H23N1Na1O6 | Assigned | 4 |
| C14E1H19N1Na1O4 | Assigned | 5 |
| C14E1H21N3Na1O6 | Assigned | 3 |
| C14E1H22N3O6 | Assigned | 3 |
| C15E1H25N4O5 | Assigned | 2 |
| C16E1H20N2Na1O4 | Assigned | 6 |
| C17E1H30N2Na1O8S1 | Assigned | 8 |
| C7E1H13N1Na1O4 | Assigned | 3 |
| C8E1H15N1Na1O4 | Assigned | 5 |
| C8E1H15N1Na1O5 | Assigned | 3 |
| C9E1H15N1Na1O6 | Assigned | 3 |
| C9E1H17N1Na1O4 | Assigned | 5 |
| C9E1H17N1Na1O5 | Assigned | 3 |
| C10E1H19N1Na1O4S1 | Assigned | 4 |
| C18E1H29N4O7 | Alternative Assignment | 2 |
| C14E1H24N2Na1O8S2 | Not Assigned | N/A |
| C14E1H26N2Na1O6 | Not Assigned | N/A |
| C15E1H26N2Na1O8S1 | Not Assigned | N/A |
| C16E1H28N2Na1O8S2 | Not Assigned | N/A |

Furthermore, this methodology can be extended to sets of detected EMF cliques (super-cliques) representing different chemical derivitizations of a specific metabolite. Differences in the EMFs reflect additions of known chemoselective tags and/or adducts to specific metabolites represented by the EMF of the base clique. A goodness-of-fit score can be calculated for super-cliques of known derivitizations. Furthermore, a comparison of the matrix of log intensity ratios for specific cliques can be used to identify super-cliques of unknown derivitizations.

The present invention, in one form thereof is directed to a method for mass spectrometry data analysis for identification of a specific elemental molecular formula (EMF) for an unknown compound. The method includes calculating a natural abundance probability (NAP) of a given isotopologue for isotopes of non-labeling elements of an unknown compound and creating and sorting caches of molecular fragments for a subset of isotopes identified using the NAP, into a requisite cache data structure, to be searched. Peaks from raw spectrum from mass spectrometry for an unknown compound are characterized and sample-specific peaks are separated from various spectral artefacts seen in ultra-high resolution Fourier transform mass spectra. Sets of possible isotope-resolved molecular formulae (IMFs) are created by iteratively searching the molecular fragment caches and combining with additional isotopes and then statistically filtering the results based on NAP and mass-to-charge (m/z) matching probabilities. An unknown compound is identified and its corresponding EMF determined from statistically-significant cliques of isotopologues with compatible IMFs.

The present invention is another form thereof is directed to a system of mass spectrometry data analysis for identification of a specific elemental molecular formula (EMF) for an unknown compound. The system includes computer memory adapted to store mass spectrometry data for an unknown compound and a computer processor adapted for performing analytics on mass spectrometry data from mass spectrometry for the unknown compound. The processor calculates a natural abundance probability (NAP) of a given isotopologue for isotopes of non-labeling elements of an unknown compound. Further, the processor creates and sorts caches of molecular fragments for a subset of isotopes identified using the NAP, into a requisite cache data structure, to be searched. Next, peaks from raw spectrum are characterized and sample-specific peaks are separated from various spectral artefacts and noise seen in ultra-high resolution Fourier transform mass spectra. Further, the processor creates sets of possible isotope-resolved molecular formulae (IMF) by iteratively searching the molecular fragment caches and combining with additional isotopes and then statistically filtering the results based on NAP and mass-to-charge (m/z) matching probabilities. Finally, the processor identifies an unknown compound and its corresponding EMF from statistically-significant cliques of isotopologues with compatible IMFs.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 2A shows Thermo Orbitrap Fusion Tribrid FTMS spectrum mainly due to digital resolution and scan-level consistency issues and FIG. 2B shows Bruker SolariX XR ICR FTMS spectrum mainly due to ringing artefacts derived from truncation issues in the Fourier transformation.

FIGS. 4A-4C are graphs demonstrating limitations in digital resolution and scan-level inconsistencies leading to peak m/z offsets in a Thermo Orbitrap Fusion Tribrid FTMS spectrum in which FIG. 4A shows average spectrum for a peak across all transients, FIG. 4B is a set of 11 transient scans, and FIG. 4C shows highest intensity point for each scan.

FIG. 6A fuzzy sites, FIG. 6B ringing, and FIG. 6C partial ringing.

FIGS. 9A and 9B show that minimal ion intensity effects are observed after peak characterization, in which FIG. 9A shows regression of normalized NAP versus relative intensity, and FIG. 9B is a histogram of log NAP ratios minus log intensity ratios.

FIG. 13A lists chemical substructure model representing the possible number of $^{13}$C incorporation from $^{13}$C$_6$-Glc tracer into UDP-GlcNAc, accounting for the observed FT-ICR-MS isotopologue peaks.

DESCRIPTION OF EXEMPLARY EMBODIMENTS

Figure 1A:
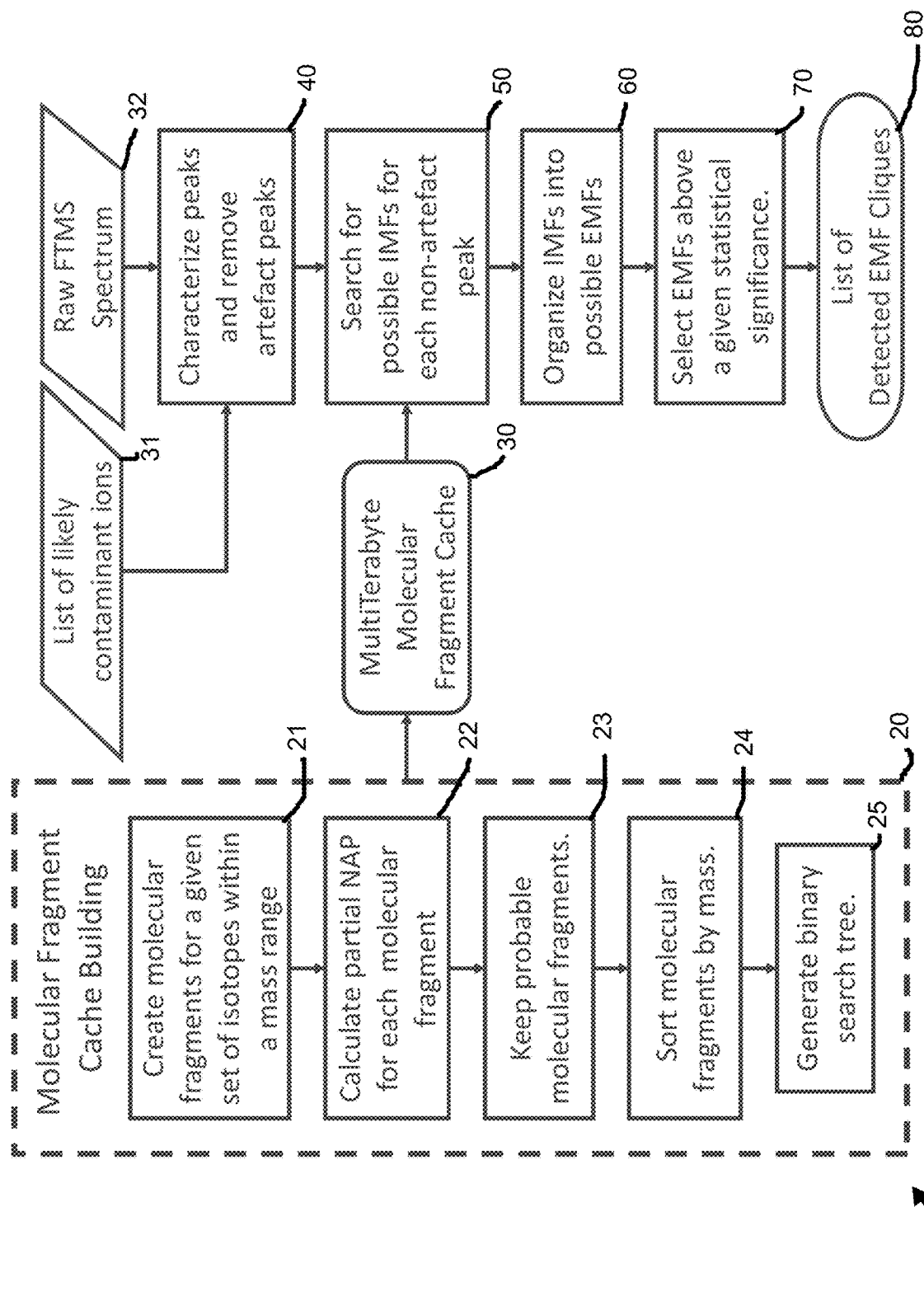
FIG. 1A is a flowchart showing a metabolite identification process using ultra-high resolution mass spectrometry in accordance with the present invention.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

Although any methods, devices, and materials similar or equivalent to those described herein can be used in the practice or testing of the presently-disclosed subject matter, representative methods, devices, and materials are now described.

Metabolomics can be described as the study of collections of metabolites, both intermediate and end products of cellular processes. Living cells are maintained under non-equilibrium conditions, which requires constant input of energy. The cells must also maintain their infrastructure, and perform tissue-specific tasks, all of which need energy and raw material. Metabolism is the set of processes that convert exogenous compounds to metabolic energy, which drives biochemical reactions within the cell, maintains homeostasis, provides the means to do work (e.g. contraction, movement, action potentials, secretion and so forth), for cellular repair, and to divide. Metabolism responds to exogenous signals as represented by diet and pollutants for example, and local environments (microenvironment) as represented by the conditions prevailing outside cells in tissues. As such, metabolism is a sensitive indicator of pathology, and the ability to measure global metabolism in quantitative detail is of fundamental importance in all aspects of biology. Practical examples include prediction and identification of disease state and prediction of response to therapeutics.

Metabolomics tools provides the technical means to carry out global analyses of metabolism, by identifying and quantifying a large fraction of all of the metabolites present in a cell, and how they change in response to perturbations within relevant metabolic networks. Metabolomics therefore requires high-end analytical instrumentation, including mass spectrometry (MS).

While global metabolomics, including the quantification of a large number of metabolites in tissue or biofluids, can identify disease states or response to therapeutics by reference to the normal condition, determining specific mechanisms, such as detecting which pathways are impacted in particular cell types within a tissue by measuring metabolic fluxes, requires additional information. Indeed, many metabolites are present in different amounts in different cell types or within compartments of cells, as well as participating in several pathways simultaneously. To identify precursor-product relationships, it is necessary to distinguish different sources of carbon, nitrogen etc. which necessitates some means of "labeling" individual atoms so that their fate can be traced through metabolic pathways. Traditionally this was achieved using radioisotopes. However, stable isotopes have several advantages, including being wholly biocompatible, and also individual atoms within a metabolite are easily distinguishable by NMR and mass spectrometry.

Stable Isotope Resolved Metabolomics (SIRM) is an approach that has been developed, which combines the power of global (untargeted) metabolic profiling with atom-resolved tracking of metabolites during metabolic transformations within cells, tissue or whole organisms. The cell culture, tissue, or organism is provided with a source metabolite that is enriched at any or all of the atoms with a stable isotope (like $^{13}C$ or $^{15}N$ with natural abundances 1.1% and 0.37%, respectively), and the products are analyzed by NMR and MS at different times after treatment. Such products will include isotopomers, which are isomers having the same isotopes, but differing in the location of the isotopes (e.g., $^{13}CH_3CH_2CH_2CH_3$ vs. $CH_3CH_2{}^{13}CH_2CH_3$), and isotopologues, which are sets of isotopomers with the same mass. With SIRM data in hand, specific isotopomer and isotopologue distributions in the various product metabolites can be determined, along with the total amounts of the metabolites, which together provide detailed information about the relative importance of intersecting and parallel pathways. For example, lactate can be produced directly from glucose by lactic fermentation, as well as by glutaminolysis; the relative contributions from these independent pathways is readily determined from the isotope distributions in the lactate using either $^{13}C$-enriched glucose or glutamine as labeled sources. At the same time such labeling schemes provide simultaneous information about the flow of carbon through the pentose phosphate pathway, glycolysis, hexosamine pathway, the Krebs cycle and lipid biosynthesis among others.

Recent advances in metabolomics technologies, such as SIRM, which combine the complementary isotope-sensitive techniques of MS and NMR, enable rapid detection of tens of thousands of isotopologues and isotopomers representing thousands of metabolites; however, the necessity for metabolite identification, quantitative analysis, and interpretation, within the context of relevant metabolic networks, represents key barriers to the use of this avalanche of information-rich phenotypic data. In fact, over 50% of detected metabolites represented by cliques of detected spectral features remain unidentified in ultra-high resolution mass spectra. Therefore, the present inventors have developed a system and method that determines the isotope-resolved molecular formula for metabolites detected via sets of related isotopologues from mass spectra of samples that have been labeled with specific stable isotopes like $^{13}C$, $^{15}N$, and $^2H$ from a given labeling source and/or from natural abundance.

The presently-disclosed subject matter includes methods and systems that allow for identification of metabolites that are detected using MS. Methods and systems of the presently-disclosed subject matter can involve processing and/or obtaining MS data. In some embodiments of the presently disclosed subject matter, the metabolites are identified has having a particular element-specific molecular formulae (EMFs). In some embodiments, the metabolites are identified has having a particular isotope-specific molecular formulae (IMFs).

Figure 1B:
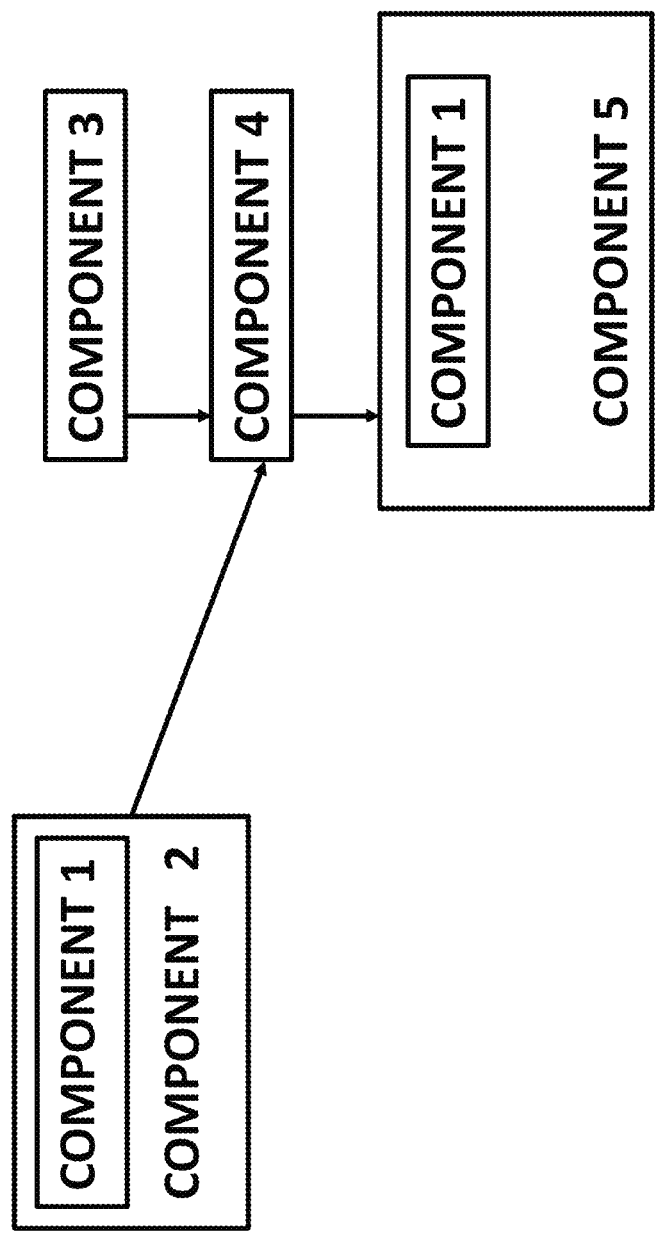
FIG. 1B is a schematic showing how five components of the identification process interact with one another to identify an unknown compound in accordance with the present invention.
Figure 1C:
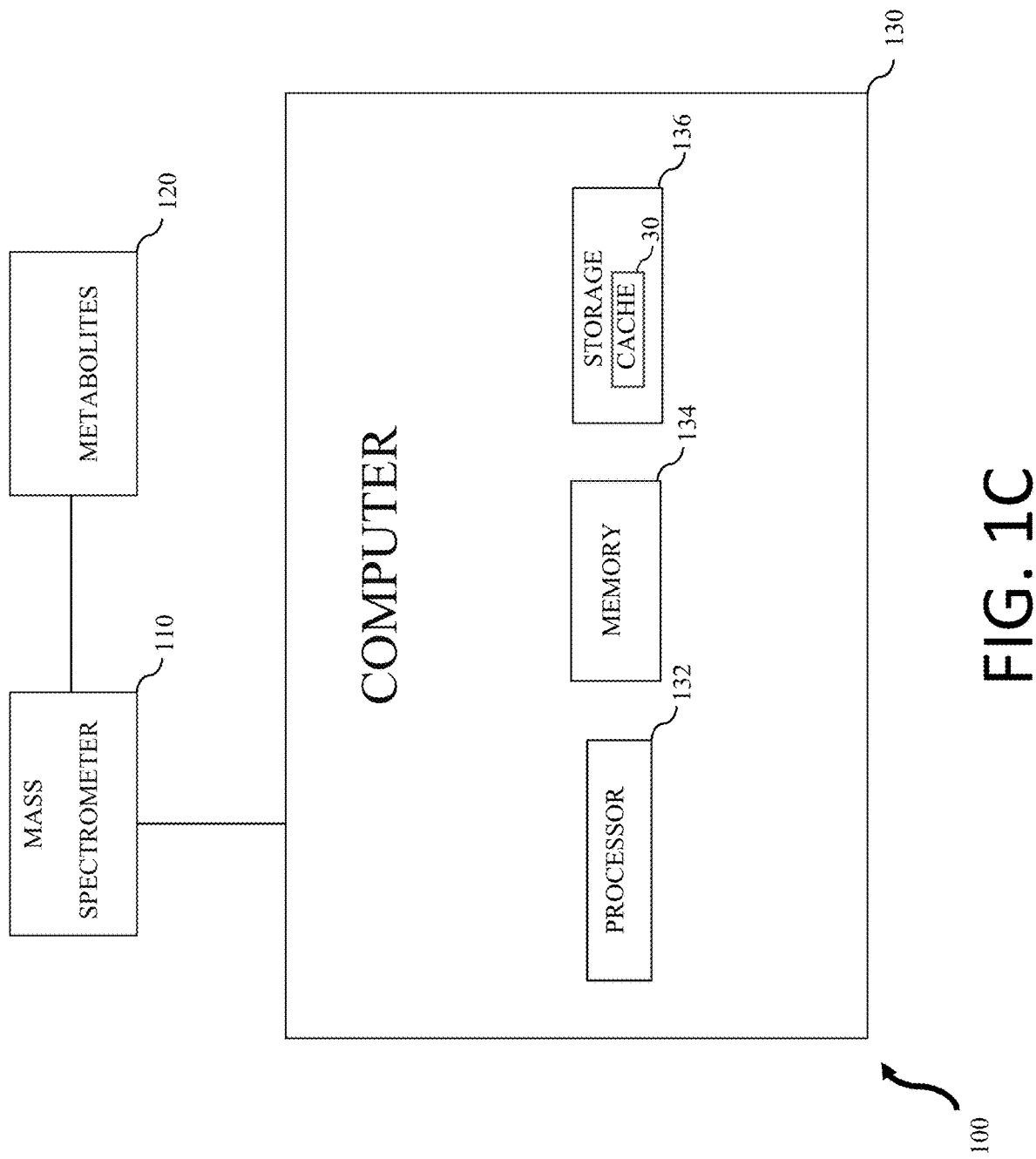
FIG. 1C is a schematic of a system for metabolite identification in accordance with the present invention.

Referring now to the present method with specific reference to the drawings, and in particular FIGS. 1A-1C. FIG. 1A is a flowchart that shows an overall high-level method in accordance with the present invention for identifying an unknown compound and FIG. 1C is a high-level schematic of a system 100 that can implement method 10. Method 10 incorporates the five (5) main components of the present method for identifying an unknown compound including metabolites. Accordingly, FIG. 1B is a high-level schematic showing how the five main components of method 10 interact to identify an unknown compound. The system 100 comprises a mass spectrometer (MS) 110 associated with a computer 130 for identifying metabolites in a sample (i.e. Metabolites 120). Mass Spectrometer 110 generates spectral data from unknown metabolites 120. The computer 130 analyzes the spectral data using a processor 132, processor memory 134 and data storage 136. While FIG. 1C shows computer 130 as containing a i) processor 132, ii) processor memory 134 and iii) data storage 136, each of these three components can be distributed across a computer network, processor 132 may comprise multiple processors connected together, and/or computer memory 134 and data storage 136 may be separate components (e.g. peripherals) operatively associated with a computer/computer processor.

A first step in method 10 is molecular fragment cache building (step 20). This includes creating molecular fragments for a given set of isotopes within a mass range (step 21). Next a partial NAP is calculated of reach molecular fragment using processor 132 (step 22). Further, based on this calculation, probable molecular fragments are kept for further analysis (step 23). Molecular fragments are sorted by mass (step 24). Finally with regard to the molecular fragment cache building (step 20), a binary-like search tree is generated (step 25) and stored in computer storage 136. Accordingly, step 20 implements Component 1 and Component 2 of the present method for identifying an unknown compound as shown in FIG. 1B. The result of all parts of step 20 is a multi-terabyte molecular fragment cache 30 that is created in computer storage 136 (FIG. 1C).

A list of known and/or possible contaminant ions (step 31) along with the raw FTMS spectrum (step 32) are converted and analyzed in step 40 to filter out real spectral peaks from analytical artefacts, chemical artefacts, and noise. The resulting real spectral peaks are characterized with respect to peak m/z, height, and normalized area across raw FTMS scans. These steps correspond to Component 3 as shown in FIG. 1B.

As one of ordinary skill in the art will appreciate, mass spectrum data may include artifacts such as contaminate ions. Accordingly, the present method 10 identifies likely contaminate ions as will be discussed below in further detail with regard to contaminate ion identification. Using raw Fourier transform mass spectrometry (FTMS) and a likely list of contaminate ions, peaks are characterized and artifact peaks removed (FIG. 1A, step 40 and FIG. 1B, Component 4) using the multi-terabyte molecular fragment cache 30 in computer storage 136. A search of possible IMFs for each non-artifact peak is conducted using processor 132 and computer memory 134 (step 50). Subsequently, IMFs are organized into possible EMFs (step 60). EMFs are selected by processor 132 that exceed a predetermined or given statistical significance (step 70). Based on this, a list of detected EMF caches are identified (step 80). This list of detected EMF caches allows one to identify the specific actual elemental molecular formula for the unknown compound such as a metabolite. Accordingly, the present method can be used to identify compounds such as the elemental molecular formula for an unknown metabolite.

In some embodiments, methods of the presently-disclosed subject matter involve assembling a large sorted cache of plausible molecular formula fragments. Such assembly can involve use of metabolite bonding pattern rules for elements in the cache. For example, the number of hydrogens is bounded by the number of carbons and nitrogens. Such assembly can also involve calculating a natural abundance probability (NAP) of isotopes of non-labeling elements (e.g., $^{13}C$ has a natural abundance of 1.1%). In some embodiments, the NAP can be calculated using the following formula: xxx $$P_E(k_1, k_2, \ldots, k_m) = \binom{E_{Max}}{k_1, k_2, \ldots, k_m} \prod_{x=1}^{m} NA_{E_{lx}}^{k_x}$$

$$NAP = \prod_{j=1}^{n} P_{Ej}$$

This formula can be used to calculate the NAP for specific isotopically-resolved molecular formulas. In the case where a specific isotope(s) comes from a labeling source, a relative NAP is calculated where that isotope's contribution to the element's probability ($P_E$) is omitted. For isotope combinations for elements containing 3 or more isotopes, one of which is labeled, a relative NAP can be calculated using the remaining isotopes else the relative NAP is set to one.
The set of isotopes excluded from the NAP calculation depends on experimental conditions (e.g., $^{13}C$ can be used as a label/tag, but also has a natural abundance of 1.1% and will be present even when not used as a label/tag).

In some embodiments, methods of the presently-disclosed subject matter involve calculating a set of possible isotopically-resolved molecular formulae for each detected isotopologue, within a specified accuracy tolerance. Such isotopologues can be detected, for example, by a particular m/z ratio peak by MS. Such calculation can involve assembling specific isotopically-resolved molecular formulae, and filtering such formulae, for example, using calculated NAP, calculating m/z matching probability, a statistical measure of how well the molecular formula matches the m/z ratio, and using metabolite bonding pattern rules.

In some embodiments, methods of the presently-disclosed subject matter involve identifying a metabolite isotopologue-offset clique, which is a clique of isotopologue and offset peaks associated with a specific elemental molecular formula. Such identification can involve identifying compatible isotopically-resolved molecular formulae for pairs of isotopologues, by comparing their sets of isotopically-resolved molecular formulae and identifying an intersection between the sets. Each intersecting pair of complementary isotopically-resolved molecular formulae that correspond to the same elemental molecular formula and have equal numbers of labeling isotopes are statistically evaluated. Such evaluation can make use of both m/z matching probabilities and calculation of a log-ratio match probability, which is a log ratio of isotopologue peak intensities statistically compared to the log ratio of each isotopically-resolved molecular formula NAP. Each compatible intersecting pair of isotopically-resolved molecular formulae represents evidence for specific elemental molecular formulas in a mass spectrum. Specific elemental molecular formulae are identified by statistically evaluating the sum of compatible intersecting pairs of isotopically-resolved molecular formulas that support the same elemental molecular formula.

In some embodiments, methods of the presently-disclosed subject matter involve identifying super cliques, with inter-clique differences in elemental and isotope-specific molecular formulae, in the mass spectrum. Such identification can involve comparing a pair of detected metabolite isotopologue-offset cliques using a matrix of log intensity ratios. Such differences in elemental and isotope-specific molecular formulae can reflect additions of known tags and/or adducts to specific metabolites represented by the elemental molecular formula of the base clique.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is further illustrated by the following specific but non-limiting examples. The following examples may include compilations of data that are representative of data gathered at various times during the course of development and experimentation related to the present invention.

EXAMPLES

These Examples describe studies that have been conducted and/or are contemplated, which provide for a combination of bioinformatic, biostatistical, and systems biochemical tools for the analysis of large metabolomics datasets. This integrated set of analyses will have broad application from the discovery of specific metabolic phenotypes representing biological states of interest to a mechanism-based understanding of a wide range of specific biological processes (cell growth, apoptosis, differentiation, nutrient specialization, symbiosis, etc.) with particular metabolic phenotypes.

Example 1. Develop tools for raw data analysis, error analysis, and quality control of SIRM data. The present inventors contemplate standardized procedures and tools for analyzing MS data that include peak assignment, metabolite identification, quantification, error analysis, and quality control. These tools will automate the detection and assignment of isotopologues from ultra-high resolution/accurate MS histograms. Emphasis is put on the development of methods for detecting and facilitating assignment of unidentified metabolites, as well as error analysis of isotopologue intensities. The new methods are truly innovative since they utilize the combined advantages of stable isotope labeling, new chemoselective probes being developed by collaborators, ultra-high resolution/accurate MS, allowing better integration with other sources of data, especially NMR isotopomer-specific data. The present inventors are also leveraging metabolite and spectral information in public databases to facilitate assignment via functional group and substructure searches.

Develop clique-based methods for identifying FT-MS-observed metabolite isotopologues. CREAM has implemented, in the program PREMISE [5], an algorithm for automated assignment of compounds utilizing the ultra-high resolution and mass accuracy capability of the FT-MS and has created a database of known metabolites with their exact masses calculated to 6 decimal places (accuracy and routine resolution of m/Am=400,000 @ 400 m/z). This approach, based on a single monoisotopic peak from FT-MS data, is limited both by the spectral signal-to-noise ratio and by the reliance on a database of known metabolites. A more robust approach is to use a clique of related isotopologue peaks (e.g. Mo to M17 of UDP-GlcNAc) to detect metabolites. This approach greatly reduces the false positive rates without using high signal-to-noise cutoffs, as the chance of multiple noise peaks being correlated in an isotopologue-offset clique becomes infinitesimally small with increasing clique size. Also, the detection of a self-consistent clique reduces the need for a metabolite database in the initial detection. Furthermore, detecting all metabolite cliques from an FT-MS spectrum is computationally very similar to the classical problem of listing all maximal cliques in a graph.

However, many algorithms that solve this problem require exponential computational time for their worst-case execution [11, 12]. To address these computational issues, the present inventors have designed an algorithm that makes the graph representation very sparse, allowing the use of optimal "maximal clique" methods that sidestep the computationally challenging issues inherent in classic maximal clique detection algorithms [11, 13]. Many of the computationally expensive steps of the algorithm are easily parallelizable, allowing full use of newer high-multicore (>100 cores) computer systems. The algorithm exploits the ultra-high mass accuracy (routinely 5_1 ppm) and resolution (400,000 m/Am) of the FT-MS [14] that can distinguish mass differences between isotopologues with the same nominal mass but differing isotope counts. At this resolution, a unique or near-unique isotope-specific molecular formula (e.g. $^{13}C_5{}^{12}C_1{}^1H_{12}{}^{16}O_6$ for the M5 $^{13}C$ isotopologue of glucose) can be directly calculated from the mass measured when limited to expected elements in metabolites. In the algorithm, the list of possible isotope-resolved molecular formulae is reduced to the list of elemental (non-isotope resolved) molecular formulae. Each pair of peaks within a sliding window of n Da of each other is then compared to see if their lists of elemental molecular formulae intersect. In this case, n is limited by the number of non-labeling isotopes of a particular labeling element present in the isotope-specific molecular formula. The intersection test creates a very sparse graph.

Detected metabolite isotopologue-offset cliques represent a group of isotopologues due to natural abundance isotopic distribution and/or enrichment from metabolic tracers. Quantitative analyses of isotopic enrichment require correction for the natural abundance of the isotopes (e.g. 1.11% for $^{13}C$) before application in the reconstruction of relevant metabolic networks (cf. 1.13.4). The present inventors have designed, implemented, and parallelized algorithms based on analytical solutions that correct for the effects of isotopic natural abundance [3, 15] and will apply them as a final quality control assessment for detecting metabolite isotopologue-offset cliques (cf. 1.13.2.6).

Pairwise comparisons of detected metabolite isotopologue-offset cliques will be used to identify super-cliques across multiple related FT-MS histograms (e.g. ±different chemoselective (CS) tags, ±CS isotope encoding, ±adducts, or ±labeled tracers), with inter-clique differences in both elemental (e.g. C6H1206) and isotope-specific molecular formulae. These differences reflect additions of known CS tags, adducts, or labeled atoms to specific metabolites represented by the monoisotopic mass or base clique. Reducing computation to pairwise clique comparison of elemental and isotope-specific molecular formulae is both very efficient and easily parallelizable. Thus, super-clique detection will identify a list of functional groups or enriched isotopologues associated with each base clique.

Develop methods to deal with unidentified metabolites. There are two kinds of unidentified metabolites in these datasets. The first is an assigned metabolite that has not been placed into known metabolic networks. The second kind is a detected compound where only its molecular formula and certain chemoselected functional groups have been assigned. To address both kinds of unidentified or partially assigned metabolites which make up a majority of current SIRM and other metabolomics datasets, the present inventors contemplate the development of methods that map structurally similar compounds onto known metabolic networks, starting with versions available from KEGG Pathway [31], to determine hot spots of similarity (clusters) and calculate a probability or likelihood of placement. Metabolic network correlations between similar compounds represent hypotheses for where newly discovered metabolites may fit within metabolic networks of interest. In this regard, tools have been implemented that download the metabolic networks in KEGG Pathway into a local MySQL database which will be converted into a SQLite database. This mapping of compounds can be done for similar matches from HMDB and KEGG Compound or exact matches from ChemSpider.

This mapping onto metabolic networks creates an additional filter on ChemSpider results that removes organic compounds with no significant similarity score to compounds in the metabolic networks and thus are not expected to exist in general cellular metabolism. Also, mappings will be very sparse with respect to the metabolic network, except in rare cases that a metabolite is very similar to a common cofactor or coenzyme like ATP. Therefore, a simple greedy node inclusion algorithm should suffice to identify hot spots. More sophisticated clustering methods will be investigated if needed. Ranking of hot spots will be based on a scoring method like the summation of node similarity multiplied by the highest similarity score in the hot spot. The centroid node and size of the hot spot may be additional useful features to calculate. Furthermore, this general methodology should be amenable to correlated cliques of unidentified or partially identified metabolites and not just a single unidentified metabolite. Correlated cliques of metabolites will be derived from covariance analyses across a time series of MS experiments (cf. 1.13.3.2).

However, there is a general assumption made by the above approach: unidentified metabolites are structurally similar to metabolites in known metabolic networks. This may not be true in some instances. An alternative approach is to take a correlated clique of unidentified metabolites and i) identify exact matches in ChemSpider for each unidentified; ii) structurally compare these exact matches between the unidentified; and iii) find the most common substructure that best spans the clique of unidentified metabolites. This refinement into a common substructure may improve mapping onto metabolic networks, especially when combined with additional correlation data. At the very least, this approach provides hypotheses of the chemical structures or substructures of the unidentified. Finally, open source tools like Cytoscape [32, 33] will be used to generate graphics that visualize the results from these approaches. Cytoscape is a general tool for visualizing networks and other graphs and is an excellent choice for visualizing hot spots of similarity within metabolic networks. In addition, common substructure similarity across a clique of metabolites can be represented as a graph using this tool.

Develop dataset-based and clique-based error analyses for quality control and evaluation of error propagation. The purpose of the above described methods is to reduce raw spectroscopic data in fully and partially identified lists of metabolites, with their isotopomer/isotopologue intensity distributions quantified, especially across a series of related spectra and histograms. Since FT-MS histograms typically take only 5 minutes to collect for a dataset containing tens of thousands of isotopologue peaks, it is relatively straight-forward to measure and calculate both absolute and relative peak intensity variance across analytical replicates. From a quality control perspective, an abnormally high analytical replicate variance can indicate problems with the analytical platform or sampling handling. Both possibilities should be tested, especially when low signal-to-noise ratios are detected. After accounting for analytical variance, the remaining variance across biological replicates is often interpreted as being of biological origin, especially when mixed model methods are utilized [34].

Figure 10:
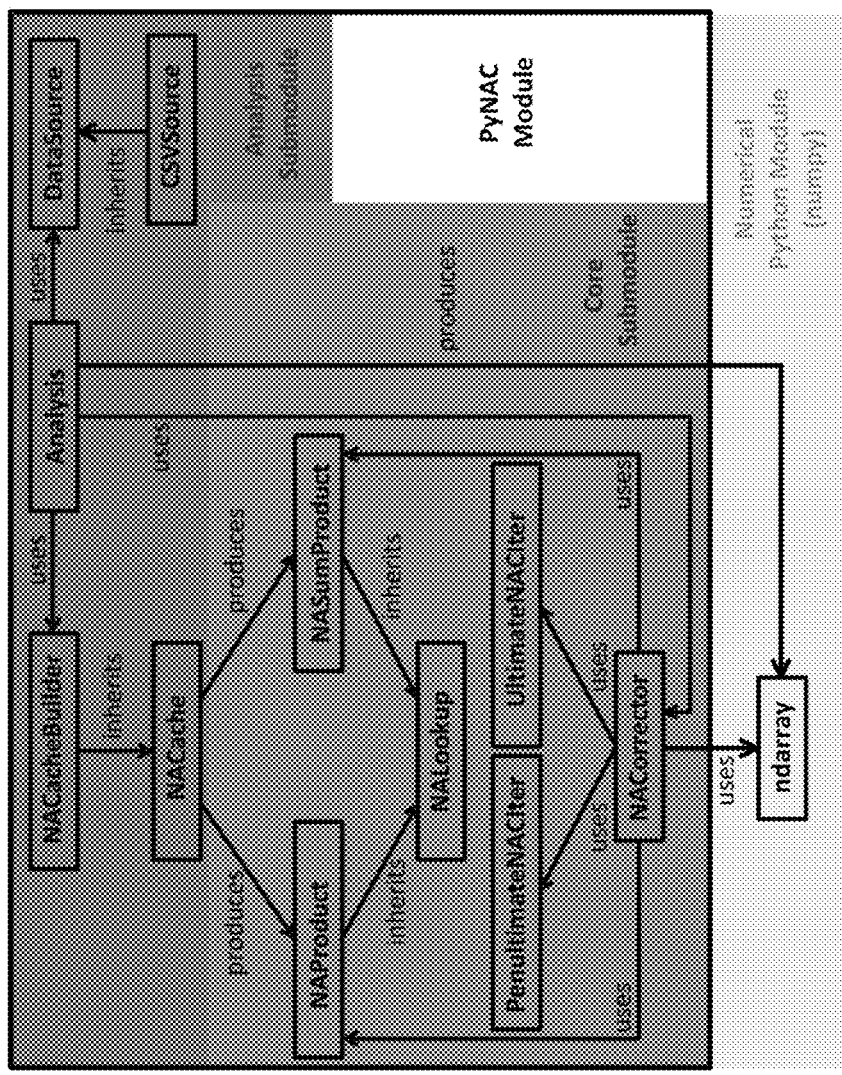
FIG. 10 is a diagram illustrating class relationships and modularization of parallelized natural abundance (NA) correction algorithm.
Figure 11:
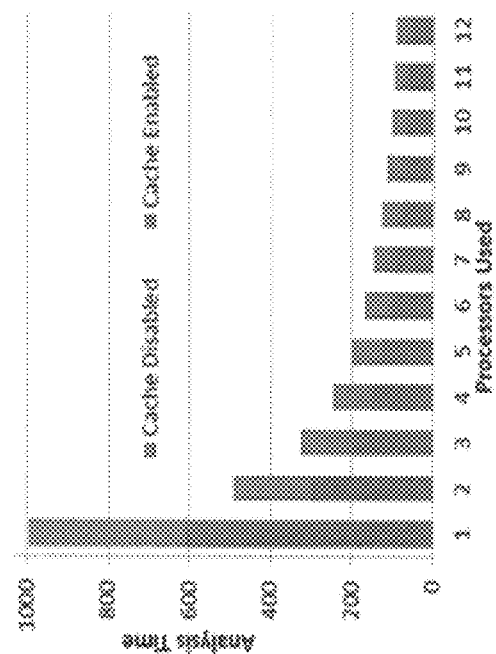
FIG. 11 is a graph showing improvement in multiprocessing NA correction running time with increasing numbers of processors used.

However, thanks to the presence of isotope labeling due to natural abundance (NA), correction of natural abundance can also be used to calculate error at the level of a specific detected metabolite isotopologue-offset clique. These $^{13}C$ and $^{15}N$ natural abundance correction algorithms have been implemented based on the present inventors' derived analytical solution [3-5]. From rigorous tests on simulated datasets, these iterative correction algorithms propagate only half of the error expected from the non-iterative analytical solution. Moreover, with reference to FIGS. 10 and 11, due to the excellent parallelized design and optimization of these algorithms, NA correction in a typical isotopologue dataset (50000 peaks organized into 9066 metabolite isotopologue-offset cliques) dropped from over 600 seconds for a single core to less than 50 seconds with multiprocessing for 12 cores on a Linux machine with dual Intel Xeon Processors X5650 (each processor has 6 cores). Because of this parallelized improvement in running time, a clear and computationally practical path is seen for estimating various types of systematic error via simulation for each analytical replicate at the level of each detected and identified isotopologue. This is done by a comparison of varied amounts of simulated systematic and nonsystematic error between metabolite isotopologue-offset cliques within a single analytical replicate. When combined with an analysis across multiple analytical replicates, total replicate variance can be separated into systematic and nonsystematic components. This approach could allow a very significant correction in systematic error and a large reduction in analytical replicate variance and in propagated error in downstream analyses.

Example 2. Develop basic biostatistical analysis of refined data. The present inventors are developing basic biostatistical analyses and visualizations of SIRM datasets that: i) support the optimal design of SIRM-based experiments with sufficient statistical power and ii) promote sound metabolic interpretation of SIRM data. Specifically, statistical power estimation tools for common SIRM experimental designs are contemplated, especially matched case-control paired experimental designs, which have better statistical power. More advanced statistical and machine learning methods will also be used to assess sample discrimination and classify samples with respect to biological states and conditions of interest.

Correlated metabolite clique analysis. Again using optimal "maximal clique" identification methods [37, 38], the present inventors will identify positively correlated sets of isotopologues and isotopomers and metabolite-specific chemical moieties representing relative flux. The focus on correlated metabolite cliques is pragmatic for maintaining a low false discovery rate (FDR) [39, 40] and preventing type I errors, which is achieved by using the correlated cliques to estimate covariance, effectively reducing the dimensionality of the datasets. This is especially important for subsequent analyses that deal with sample classification and mechanism-based hypothesis generation. When matched case-control datasets are being analyzed, the correlation will be calculated using the difference in the normalized isotopologue intensity or chemical moiety parameter value. The covariance error matrix will be calculated from a set of analytical replicates and this matrix will be used as a weighting factor to compensate for the non-independent error expected with these highly correlated datasets [41]. The significance and statistical power of correlated metabolite cliques will be evaluated with respect to intra-clique-correlation, correlation to specific metabolic pathways, and effect sizes (for matched case-control datasets). Criteria will be used based on a combination of these measures along with a minimum clique-size to limit which cliques are accepted as meaningful metabolic phenotypes and used to build classification models. The criteria needed for a desired false discovery rate (FDR) will be empirically estimated via a series of simulations where a large number of random datasets are created and analyzed using expected correlations from known metabolic pathways, the levels of variance in experimental datasets, and the size of experimental datasets. This approach has been found to be valuable for significance testing in identifying relevant GO terms [42].

General statistical analysis and visualization. Packages in the R statistical programming language are currently used for common statistical analyses such as mean, median, standard error, range, 95% CI, t-test in its various variants, ANOVA, general linear regression, logistic regression, and statistical power calculations. To identify significant differences, the ratio (using threshold ratio) of the control and perturbed groups will be compared using Fisher's Exact test [43] and then logistic regression will be used to model and test the effect of other covariates such as age and gender. Metabolites will also be compared using GLM procedures, including covariates such as age, gender, polyploidy where relevant. Correlation clustering methods are particularly good at handling high dimensional datasets [44].

A variety of tools available in Python and R and elsewhere are used to visualize datasets in a variety of ways. Principal Components Analysis (PCA) is used to visualize information content and its dimensionality with respect to variance. Partial least square discriminant analysis (PLS-DA) and newer OPLS-DA methods [45] will be used to assess class separability of samples, even if implementation of a version of OPLS-DA is required (currently no released R or Python package appears available). 3D data displays and heat maps will be used to visualize correlations among detected isotopologues and categories of samples as derived from various clustering methods. The new R-based tool NeatMap that generates heat maps from non-clustering methods like PCA [46] will be used, allowing side-by-side comparison with results from clustering methods. Open source tools like Cytoscape [32, 33] will be used for network visualization.

Construction of classification models. Using both refined metabolite data and accepted metabolite cliques, prediction and classification models will be built and evaluated using a variety of model building methods. Following a visual review of the data with PLS-DA and OPLS-DA [47, 48], machine learning methods will be used, including random forest [49, 50] and support vector machines with kernel selection [51, 52]. These machine learning methods are better at dealing with nonlinear correlations that may be present in a dataset. Moreover, random forest excels at multi-category classification. Various PLS-based, kernel-based OPLS [53], and machine learning methods are implemented as packages in R.

Example 3. Develop metabolic network reconstruction, moiety deconvolution tools, and omics-level data integration for mechanism-based analysis of biological processes. The present inventors will build upon manual approaches that interpret SIRM data within the context of relevant metabolic networks and facilitate mechanism-based analysis of correlated metabolites. Specifically, tools are being developed that will automate reconstruction of metabolic networks that are relevant for the interpretation of SIRM time-series experiments and SIRM datasets will be deconvoluted to determine relative pathway fluxes through these networks. The resulting pathway-specific information will serve as a point of integration and cross-validation with genomics, transcriptomics, and proteomics data, enabling interpretation of metabolic phenotypes within the context of specific metabolic and signaling pathways that are part of biological processes of interest. This context-specific interpretation will generate mechanism-based hypotheses and additional tools for their testing.

The present inventors are developing a combination of methods that will: i) analyze the relative isotope incorporation and perturbation of correlated metabolites of interest derived from raw data analyses and biostatistical analyses described above with respect to specific pathways within metabolic networks; ii) integrate this pathway-specific metabolomics information with genomics, transcriptomics, and/or proteomics data; and iii) facilitate relative flux interpretation and full metabolic flux analysis of moiety deconvoluted data within the context of specific metabolic and signaling pathways within biological processes of interest. The heart of these new methods are the moiety modeling methodologies and tools [1, 10] designed to deconvolute SIRM datasets. Non-steady-state experimental conditions are an unavoidable reality for most eukaryotic SIRM datasets, since true isotopic steady state is difficult or impractical to achieve, especially in animal systems. The moiety modeling methods are designed to handle the specific information-rich, isotopic non-steady-state conditions of these experiments. From these analyses, the present inventors can derive pathway-specific relative flux and perturbation detailing the functional significance of particular metabolic phenotypes of interest. Application of these methodologies entails the following:

Integration and refinement of organism-specific metabolic information.

Moiety model creation.

1. Moiety model optimization and selection.
2. Quantitative pathway analysis and relative pathway flux interpretation.
3. Integration with genomics, transcriptomics, and/or proteomics data.

Figure 12:
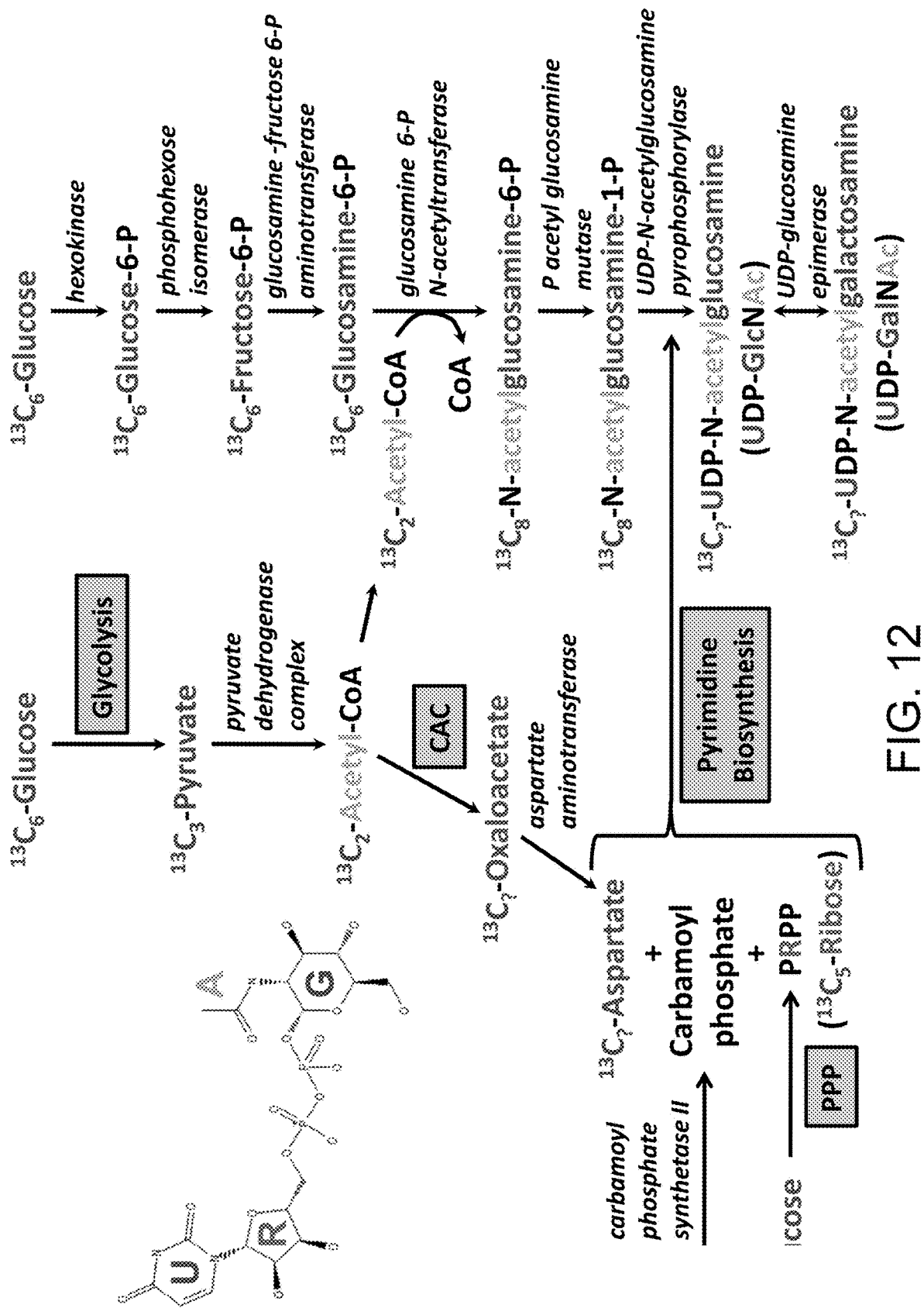
FIG. 12 depicts pathways from [U-$^{13}$C]-glucose to the four biochemical subunits of UDPGlcNAc. Glucose moiety is incorporated directly. Acetyl moiety is incorporated via glycolysis. Ribose moiety is incorporated via the pentose phosphate pathway. Uracil moiety derives from acetyl-CoA via the citric acid cycle to form aspartate where it is combined with carbamoyl phosphate.
Figure 13B:
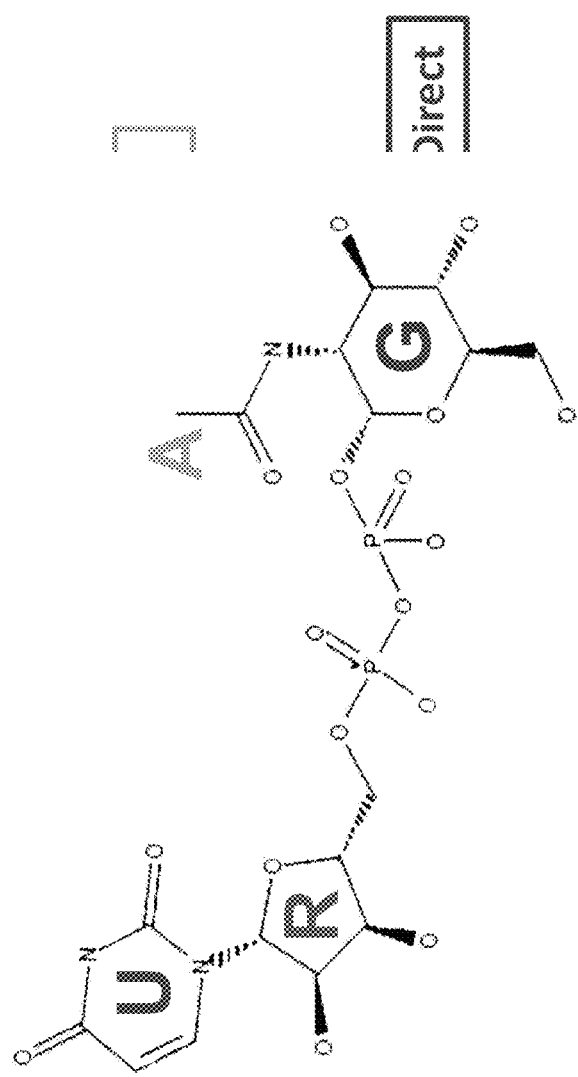
FIG. 13B shows the structure of UDP-GlcNAc annotated by its chemical substructures and their biosynthetic pathways from $^{13}$C$_6$-Glc. NAc-Glucose utilizes Gln as the nitrogen donor.
Figure 13C:
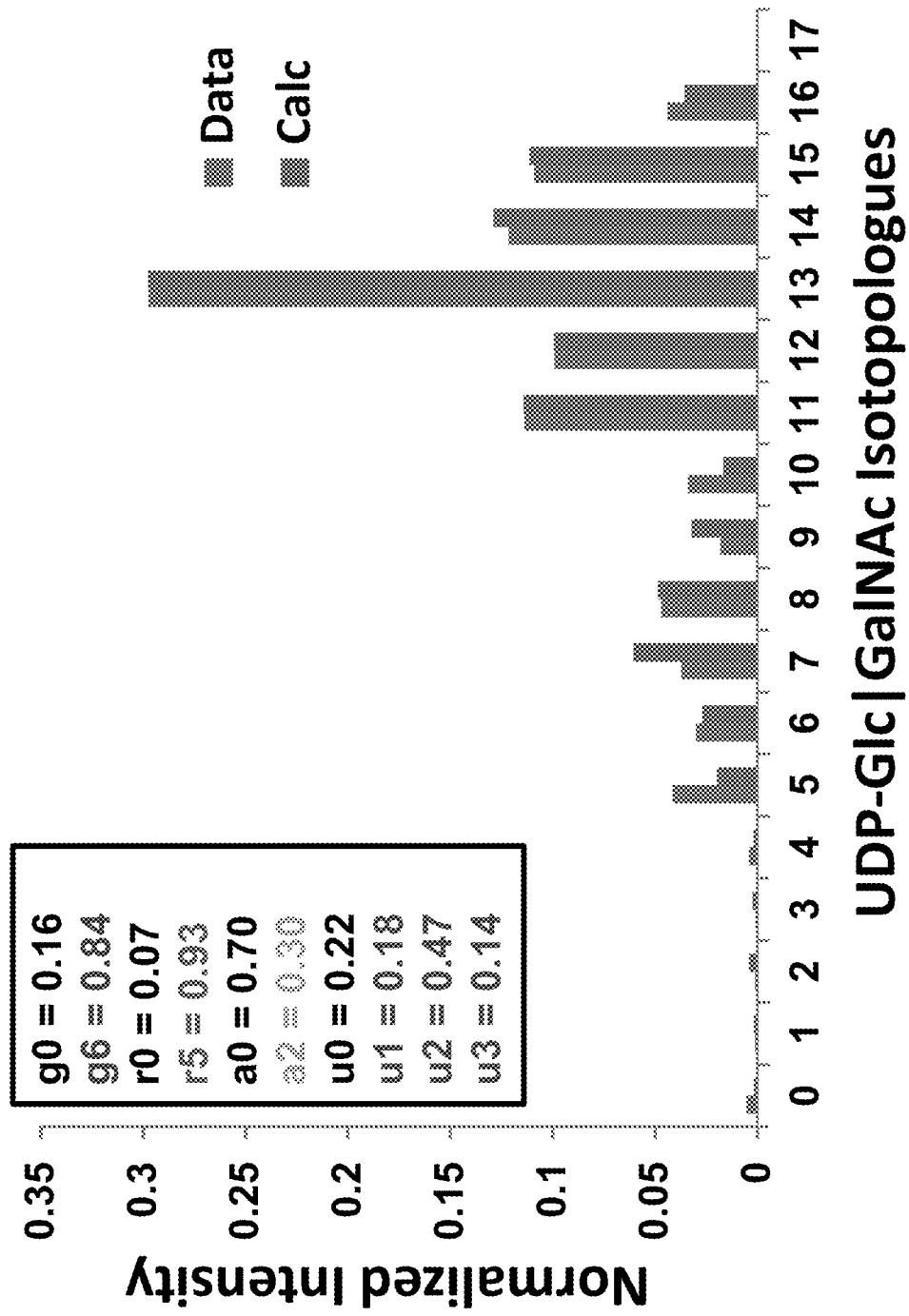
FIG. 13C is a graph showing fit of optimized chemical substructure model parameters to F-ICR-MS isotopologue data of UDP-GLcNAc extracted from human cell culture after 48 hr of growth in $^{13}C_6$-Glc.
Figure 14:
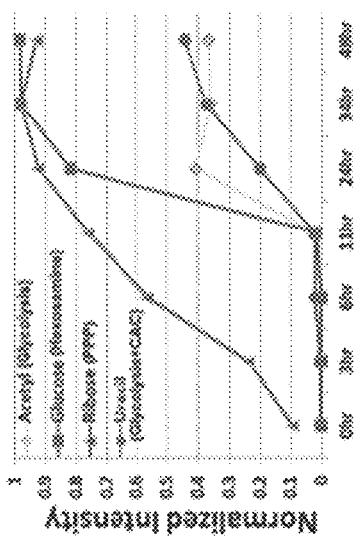
FIG. 14 is a graph illustrating a deconvoluted time course of FT-ICR-MS isotopologue peaks of UDP-GlcNAc from human cell culture extract.

The approach is to extract the necessary parts of metabolic networks according to given tracer inputs. For any set of input tracers, first their transformation pathways are selected and defined as the initial network. The fates of individual atoms are traced through the initial network and major downstream pathways are included stepwise. This process is performed iteratively so that the network size is kept within a computationally feasible scale. Here, the approach with a combined NMR and FT-ICR-MS SIRM-based study on the biosynthesis of UDP-GlcNAc is illustrated[1] (cf. FIG. 12), which is a key donor for N- and O-linked protein glycosylation [54-56]. UDP-GlcNAc has a unique NMR spectrum that is resolved from UDP-GalNAc and other UDP sugars. Based on the individual components of UDP-GlcNAc (FIG. 13b) and their known biosynthetic pathways (FIG. 12), a chemical substructure model (FIG. 13a) was constructed to enable non-steady state modeling of $^{13}C$ incorporation from labeled glucose into UDP-GlcNAc. The possible $^{13}C$ labeled isotopologues (cf. FIG. 13a) deduced from the pathways and FT-ICR-MS data were then used as model parameters in a combined simulated annealing/genetics optimization algorithm implemented in the program GAIMS [1]. Fitting these model parameters to the 18 observed FT-ICR-MS $^{13}C$-only isotopologue series (m0 to m0+17, FIG. 13c), while accounting for the $^{13}C$ natural abundance, defined relative flux through multiple connecting pathways between glucose and UDP-GlcNAc (FIG. 14), without the prerequisite for isotopic steady-state [10]. Moreover, the relevant network reconstruction, moiety deconvolution, and moiety model selection simplifies and frames the metabolic flux problem that can be accurately addressed by a isotopic non-steady-state full metabolic flux analysis [57-59].

Integration and refinement of metabolic information. For the tracer-based data analysis needs, web-based tools are being developed that: i) access relevant metabolite, metabolic pathway, atom-resolved mappings, subcellular localization, and tissue-specific gene expression information from public databases and ii) combine and refine this information for mapping to relevant parts of the targeted metabolic network. These web-based tools will extract metabolic pathway information from a variety of sources including: KEGG Ligand for atom-resolved metabolic pathways for over a thousand organisms [26]; ARM for the most complete atom-resolved metabolic pathways in E. coli [60]; MetaCyc family of databases for the most complete metabolic maps [61, 62]; and Reactome for human subcellularly-localized metabolic pathways [63, 64]. With the use of the Django web framework, a database schema for an enhanced atom-resolved metabolic network based on KEGG Ligand has been implemented and is now being testing via scraping, processing, and populating with data from KEGG Ligand. This implementation allows easy portability to several different physical databases including MySQL, PostgreSQL, and SQLite, which have been directly tested during the evolution of this database schema.

However, the real problems are in obtaining useful and reliable subcellular localization annotation. Currently, the metabolic pathway databases link back to Uniprot [65, 66] which aggregates annotation at the "protein" record. Table 2 represents a preliminary analysis of the Swiss-Prot version (downloaded Mar. 5, 2012) of Uniprot showing human enzymes organized by major EC number group versus subcellular localization. However, many genes are transcribed into multiple RNA transcripts which encode different isoforms of a protein. Uniprot stores only one composite "protein" record for almost all isoforms of a particular protein gene product. All the annotations for each isoform are simply aggregated under the single "protein" record with the relationship between isoform and annotation lost. This is a problem since the most reliable annotations are in the manually curated and reviewed Swiss-Prot. Now EMBL-ENA [67-69] has annotations associated at the RNA transcript level; however EMBL-ENA includes less reliable automatic annotations. In fact, the EMBL-ENA is translated into the TrEMBL version of Uniprot which also has annotations aggregated in the "protein" record. Since TrEMBL has Swiss-Prot annotations removed to prevent duplication of annotation, the present inventors will filter EMBL-ENA against Swiss-Prot in order to produce a dataset of reliable subcellular localization annotations associated directly with its RNA transcript. This will be invaluable for later integration with transcriptomics and proteomics datasets.

TABLE 2

Human enzymes organized by major EC# group & subcellular localization annotation from Swiss-Prot.

| EC | awosouelauti | Golgi | Lysosome | Cytoplasm | Secreted | Cell Membrane | Cytoplasmic Vesicle | Nucleus | Endoplasmic Reticulum | Peroxisome | Mitochondrion |
|---|---|---|---|---|---|---|---|---|---|---|---|
| 1 | 3 | 7 | 6 | 113 | 37 | 49 | 1 | 57 | 116 | 27 | 118 |
| 2 | 1 | 195 | 7 | 473 | 37 | 292 | 20 | 360 | 137 | 10 | 130 |
| 3 | 9 | 51 | 68 | 414 | 244 | 308 | 19 | 378 | 89 | 9 | 82 |
| 4 | 0 | 2 | 0 | 29 | 2 | 22 | 1 | 12 | 7 | 6 | 16 |
| 5 | 0 | 3 | 0 | 31 | 3 | 8 | 0 | 21 | 19 | 6 | 12 |
| 6 | 6 | 9 | 9 | 153 | 1 | 41 | 10 | 90 | 27 | 7 | 58 |

Protein-protein interactions are another important type of annotation in metabolic networks and especially useful in deducing nonsymmetric catalysis of symmetric molecules, which is common in multienzyme complexes. However, protein-protein interactions are not nearly as conserved as enzymatic function and are much harder to predict. Potentially useful protein-protein interaction databases like iPfam, PIBASE, DOMMINO, and MIPS [70-73] and various prediction methods are being investigated [74-79]. Also, new semantic relationships added to Gene Ontology [80] will aid in combining localization with cellular component annotations [81].

Develop atom-resolved pathway tracing and metabolic network reconstruction methods for moiety model creation. The present inventors are drawing on classic graph theory as a starting point for developing algorithms that trace relevant short paths through metabolic networks from labeled tracers to enriched metabolite isotopologues and isotopomers. Both k-shortest paths [82] and k-shortest simple paths (loopless) [83] algorithms will be employed to trace isotope from the labeling source to every labelable atom in the assigned metabolite. Preference is given to paths that combine the largest co-tracing of atoms, which represent the flow of specific functional moieties through the metabolic network. Since the metabolomic database in KEGG for any given organism is incomplete, tracings will be used from other organisms (1000 in KEGG) as hypothetical pathways. The metabolites and labeling patterns assigned from FT-MS and NMR time series data will be used to verify or refute all plausible hypothetical pathways. Finally, detected unidentified metabolites will be placed within the reconstructed metabolic networks based on: their molecular formulae/functional groups (from FT-ICR-MS), identified substructure (NMR), time series correlations with known metabolites, and labeling patterns.

With the metabolic information described above aggregated into an atom-resolved metabolic network specific to the organism of interest, the methods being developed will be able to trace groups of atoms or chemical moieties from a labeled source molecule to an observed metabolite through numerous metabolic transformations in cellular metabolism of the appropriate organism. As with any complex network, many different tracings are possible. Currently, models are described manually using a moiety model description language [1]. Web-based tools are being developed to aid in creating moiety models. These tools will also help generate related sets of plausible moiety models from relevant metabolic pathway information. Model creation requires four separate steps: i) search for relevant plausible metabolic pathways as described above; ii) identify traceable chemical moieties; iii) identify chemical moiety labeling states (i.e. possible levels of stable isotope labeling in the moiety); and iv) generate model description. Each step will be linked by common file formats and data structures, like the chemical moiety model description language (CMMDL), composed of nested name-value pairs describing traceable chemical moieties and their possible labeling states. The CMMDL parser will be expanded to simultaneously handle multiple metabolites with cross-dependencies between moiety substructures as the moiety model creation tools are developed into fully automated versions. These improvements will eventually allow simultaneous analysis of hundreds or even thousands of metabolites.

Moiety model optimization and selection. A parameter optimization tool has been developed that uses a simulated annealing genetic algorithm to optimize chemical moiety state parameters based on experimental data for a given chemical moiety model description [1]. A specific application of this tool is illustrated in FIG. 13. Since optimizations are normally repeated many times, this tool can be run on a Linux cluster in a distributed fashion via the use of standardized queue submission protocols (openPBS/TORQUE). These facilities will be expanded to handle the parameter optimization of models involving multiple metabolites. Furthermore, hierarchical and jack-knife approaches will be developed when optimizing moiety state parameters of many metabolites. Both approaches begin with the parameter optimization of individual and small correlated sets of metabolites (correlated metabolic cliques) before optimization across larger sets of parameters. These approaches are needed to efficiently optimize parameters for thousands of metabolites simultaneously.

A robust model selection method has also been implemented using the Akaike information criterion (AIC) [84] applied to average optimized parameter values [1]. Highly plausible models and often a unique model are selected from a large possible set using the SIRM time-course data. This allows the SIRM experimental data to test hypotheses of metabolic pathways made during moiety model creation, filling in gaps in current organism-specific metabolic information. Although the preliminary results with this model selection method applied to single metabolite models indicate a very robust selection method, harder problems could arise when selecting models involving multiple metabolites. Anticipating cases where multiple models are selected, additional model comparison tools will be developed that will identify common components between chemical moiety models, which will demonstrate high confidence in these components. Furthermore, it will be necessary to apply model selection earlier in the model creation and optimization steps to prevent a combinatorial explosion in the number of multiple metabolite models that need to be tested. Very low probability branches in the model search tree can be trimmed to limit this combinatorial explosion. Moreover, submodel selection and submodel likelihood functions may be required to direct model creation when all possible models cannot be enumerated.

Quantitative pathway analysis and flux modeling. Determining the time evolution of moiety state parameters provides the means to determining pathway fluxes. From this analysis, the present inventors know the relative substructure fluxes from the labeling source to the metabolite through atom-resolved metabolic pathways identified from model selection. By comparing these multiple pathways from labeled source to detected metabolites the following can be identified: i) localized pathways in common; ii) branch points in these pathways, which often represent sites of regulation; and iii) the relative fluxes through these branches. Changes in these relative fluxes would indicate a change in the regulation at these branch points and provide significant mechanistic understanding for representative metabolic phenotypes.

Facilitating 'omics' integration and mechanism-based hypothesis generation. Perturbed pathways derived from correlated metabolite cliques and changes in relative flux will become a common point of integration and cross-validation with other omics-level coupled datasets that are obtained. As an analytical cross-validation with metabolomics, this approach is statistically more powerful than pathway enrichment analysis strategies [85, 86]. Specific protein gene products identified by this cross-validation with omics-level datasets under perturbed conditions become potential hypotheses for the perturbation mechanism. To complement this coupled-experiment approach, relevant omics-level datasets already in the public repositories like genetic variations in dbSNP [87], transcriptomics data in GEO [88, 89], and proteomics data in PRIDE [90, 91] will be analyzed. GEO search methods and dbSNP search methods are being explored.

Alternative Approaches. One problem already mentioned is the incomplete information on metabolic networks of various organisms and their compartmentation. Tools will be developed that can generate more complete metabolic pathways from other organisms and validate these hypothetical pathways using SIRM experimental data. Another known problem is that not all metabolites are in the databases. The combined molecular formula, functional group, and substructure information will be used to search ChemSpider (http://www.chemspider.com/) for candidate structures. Further analysis of NMR data and MS/MS fragmentation patterns can be used to refine this list of candidates. Another potential issue is the combinatorial explosion in chemical moiety model creation and optimization involving large numbers of metabolites. This can be addressed using a combination of approaches: i) use submodel optimization and selection to eliminate highly improbable models; ii) use metabolic clique analysis, hierarchical, and jack-knife approaches to direct model optimization and selection; and iii) distribute the parameter optimization across a large computer cluster (e.g. University of Louisville CRC). Another potential issue is building good classification models. A variety of statistical and machine learning methods can be used to find the best classifier and identify key metabolic cliques. To handle non-independent error in the datasets and the covariance in time series, a set of analytical replicates will be used to calculate an error covariance matrix. A GEE model will be used to deal with issues of covariance in the time series [92] [93].

Example 4. Metabolite Identification in Ultra-high Resolution Mass Spectrometry. The present inventors have developed and prototyped a system and method that determines the isotope-resolved molecular formula for metabolites detected via sets of related isotopologues from mass spectra of samples that have been labeled with specific stable isotopes like $^{13}C$, $^{15}N$, and $^{2}H$ from a given labeling source and/or from natural abundance.

The approach requires multiple components to overcome the inherent combinatorial problem related to finding the correct isotopically-resolved molecular formula (i.e. $^{12}C_5^{13}C_1^{1}H_{12}^{16}O_6$ versus $C_6H_{12}O_6$) out of roughly 1.1 quadrillion ($1.1 \times 10^{15}$) of possible combinations that must be searched for each isotopologue with a molecular mass of less than 2000 Daltons. The components include: i) mathematical formulas implemented in algorithms that calculate natural abundance probabilities for isotopes of non-labeling elements; ii) large sorted caches of molecular formula fragments for a subset of isotopes being searched; iii) algorithms that characterize peaks from raw a raw spectrum and separate sample-specific peaks from various spectral artefacts seen in ultra-high resolution Fourier transform mass spectra; iv) algorithms that create sets of possible isotopically-resolved molecular formulas by iteratively searching the molecular formula caches, combining with additional isotopes and molecular fragments, and statistically filtering resulting isotopically-resolved molecular formulas; v) algorithms that identify metabolite cliques and super-cliques of isotopologues via the comparison of sets of possible isotopically-resolved molecular formulas from different isotopologues that identify compatible element-resolved molecular formulas in a statistically robust manner. These components will now be discussed in more detail.

Component 1. Mathematical Formulas Implemented in Algorithms that Calculate Natural Abundance Probabilities for Isotopes of Non-labeling Elements.

$$P_E(k_1, k_2, \ldots, k_m) = \binom{E_{Max}}{k_1, k_2, \ldots, k_m} \prod_{x=1}^{m} NA_{E_{1x}}^{k_x}$$

$$NAP = \prod_{j=1}^{n} P_{Ej}$$

The above equations describe the calculation of the natural abundance probability (NAP) for specific isotopically-resolved molecular formulas. In the case where a specific isotope(s) comes from a labeling source, a relative NAP is calculated where that isotope's contribution to the element's probability ($P_E$) is omitted. For isotope combinations for elements containing 3 or more isotopes, one of which is labeled, a relative NAP can be calculated using the remaining isotopes else the relative NAP is set to one.

Component 2. Large Sorted Caches of Molecular Formula Fragments for a Subset of Isotopes being Searched.

The problem of searching for probable isotopically-resolved molecular formulas is a huge combinatorial problem that becomes intractable on even large supercomputers for molecular masses over 500 Daltons. In order to make this problem tractable, one must build a large sorted cache of plausible molecular formula fragments using the NAP from Component 1 and metabolite bonding pattern rules for the elements in the cache. The cache reduces the molecular formula search time by a ratio of the time to build the cache (typically >10,000 CPU hours) versus the time it takes to search the cache (i.e. milliseconds or better). An example metabolite bonding pattern rule is the number of hydrogen atoms in a molecular formula is bounded by the number of carbon and nitrogen atoms in the molecular formula.

Component 3. Peak Characterization and Detection of Artefactual Peaks

Figure 2B:
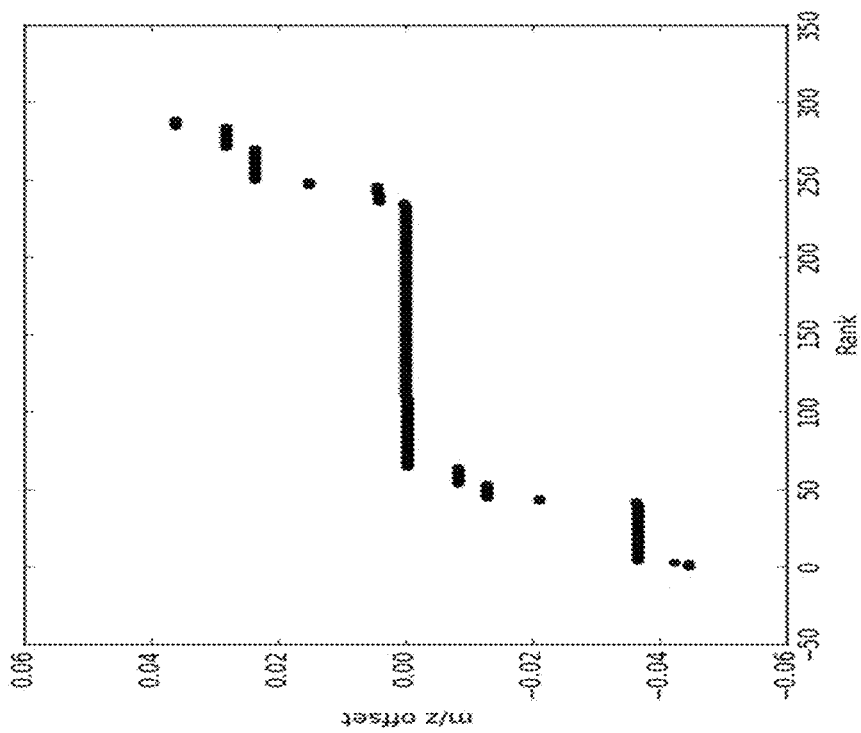
FIGS. 2A and 2B are two respective graphs showing spectra collected from Founer transform mass spectrometers showing peak m/z offset patterns detected, where
Figure 2A:
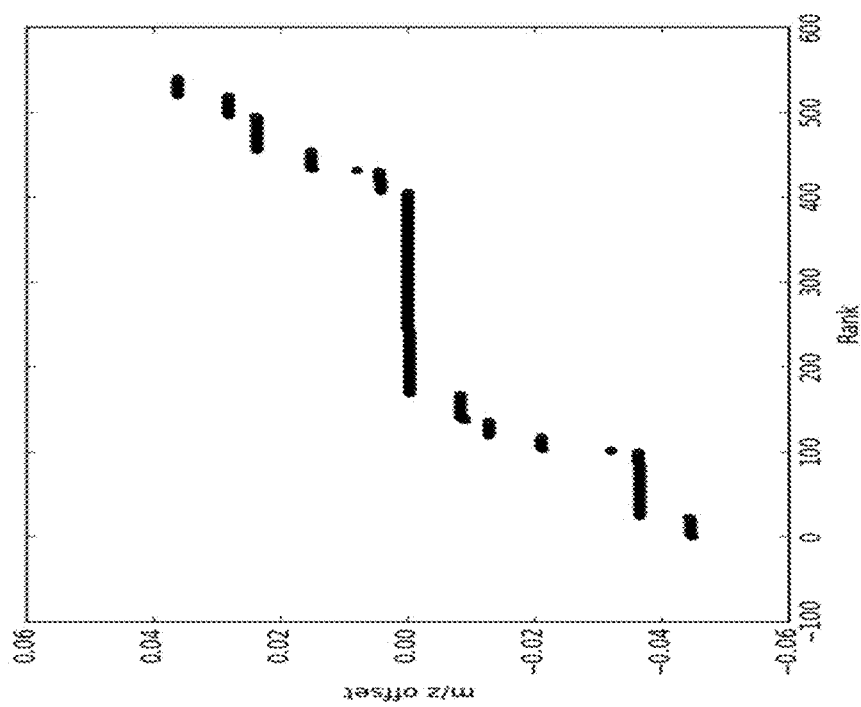
Figure 3:
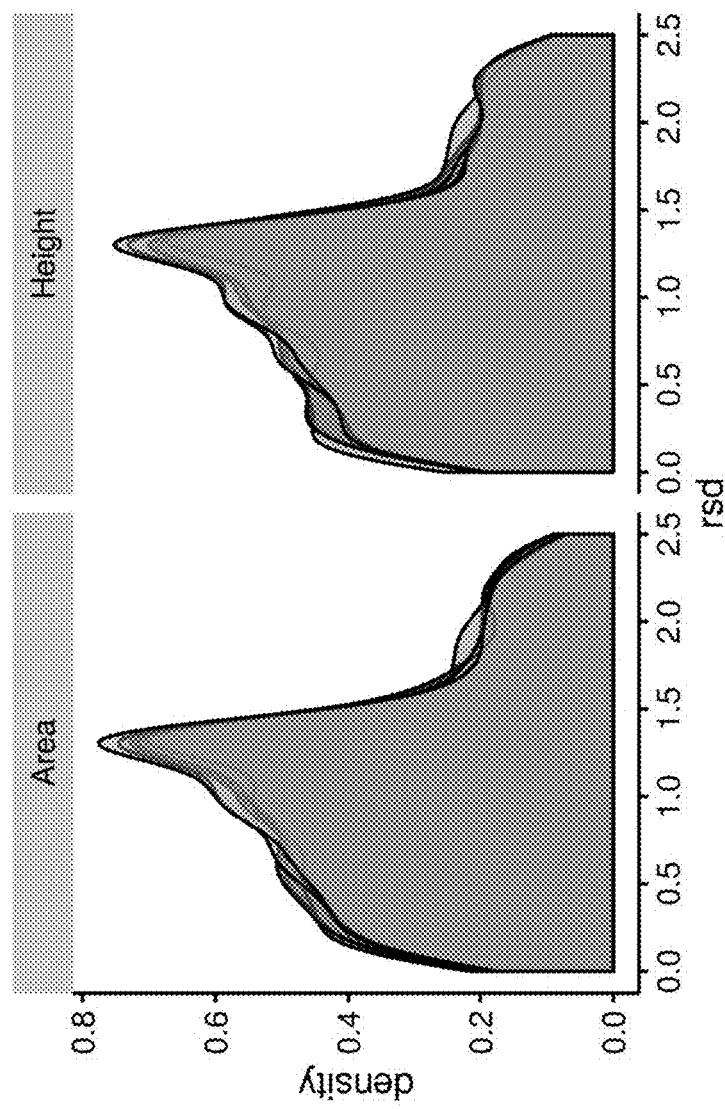
FIG. 3 includes graphs showing Relative Standard Deviation of peak heights and areas across raw scans in a Thermo Orbitrap Fusion Tribrid FTMS spectrum.
Figure 5:
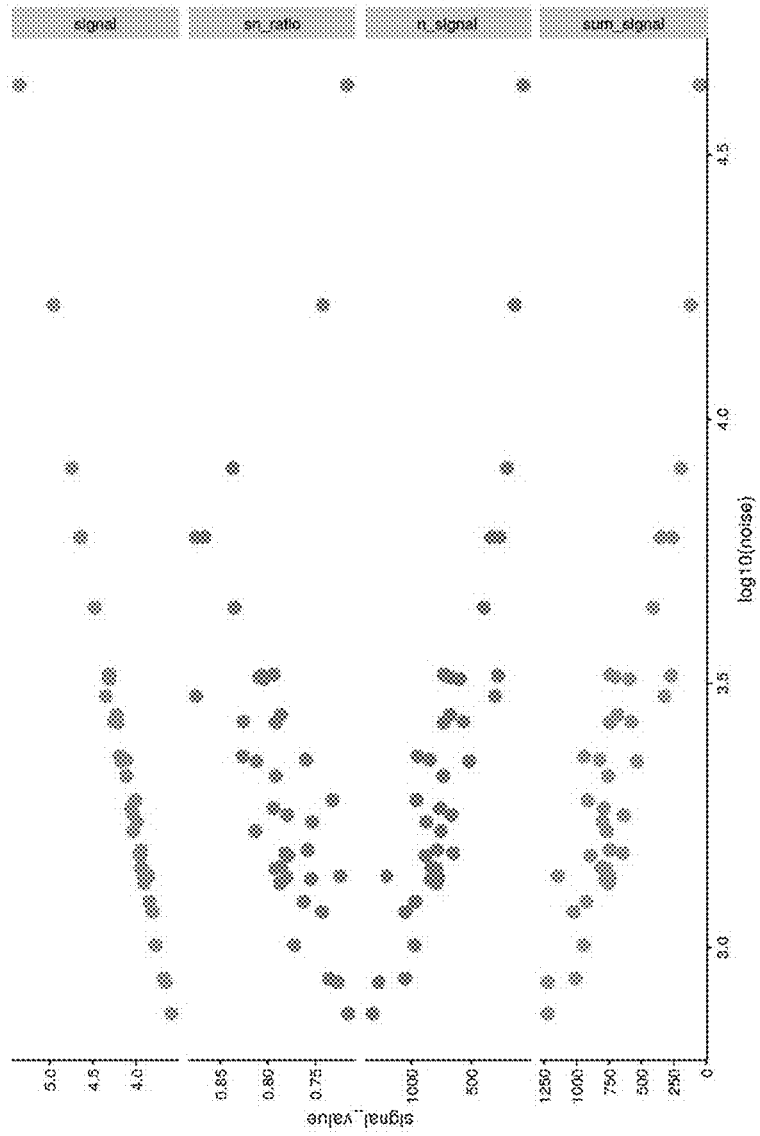
FIG. 5 shows scan-level inconsistencies in signal and noise for a Thermo Orbitrap Fusion Tribrid FTMS spectrum.
Figure 6B:
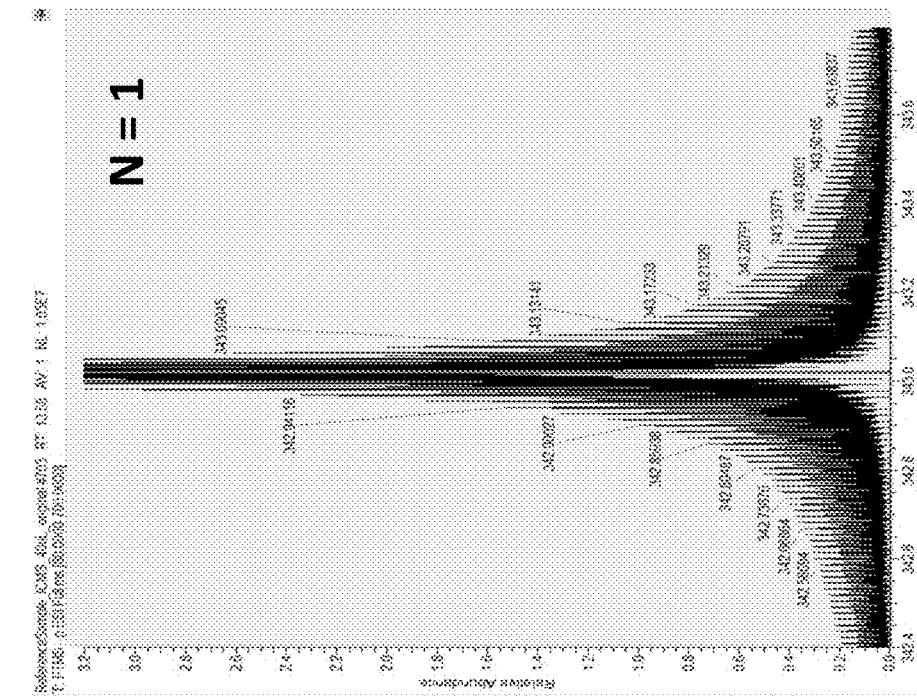
FIGS. 6A-C show three types of high peak density FTMS-based spectral artefacts.
Figure 6A:
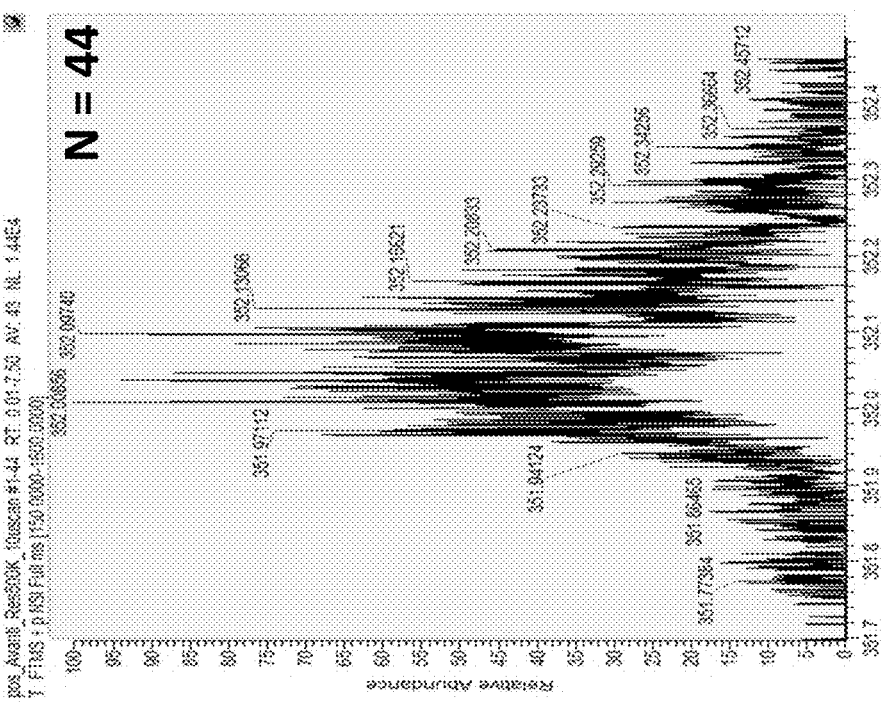
Figure 6C:
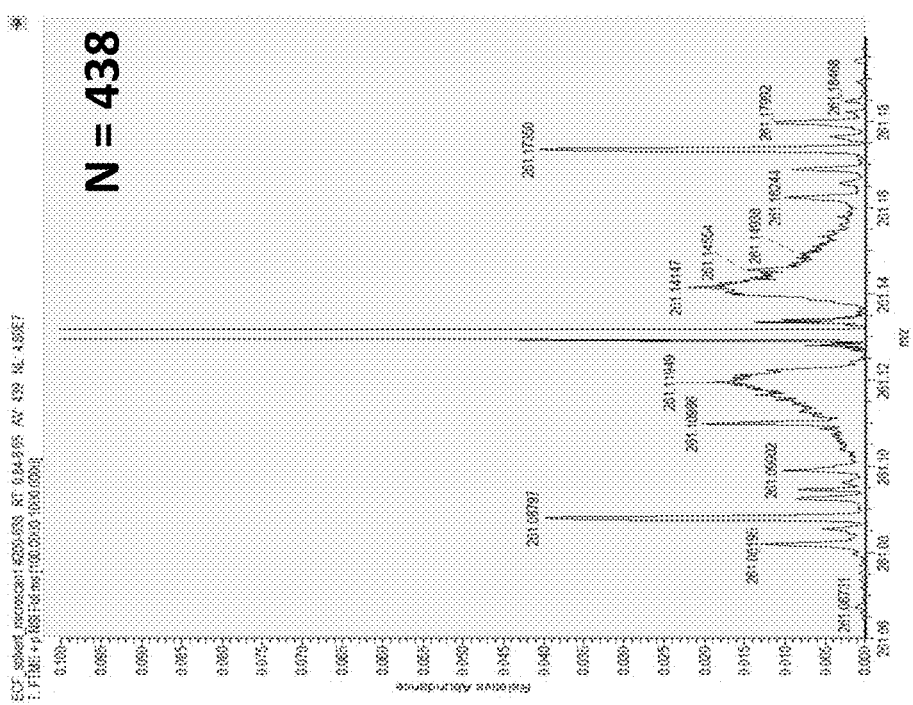
Figure 7:
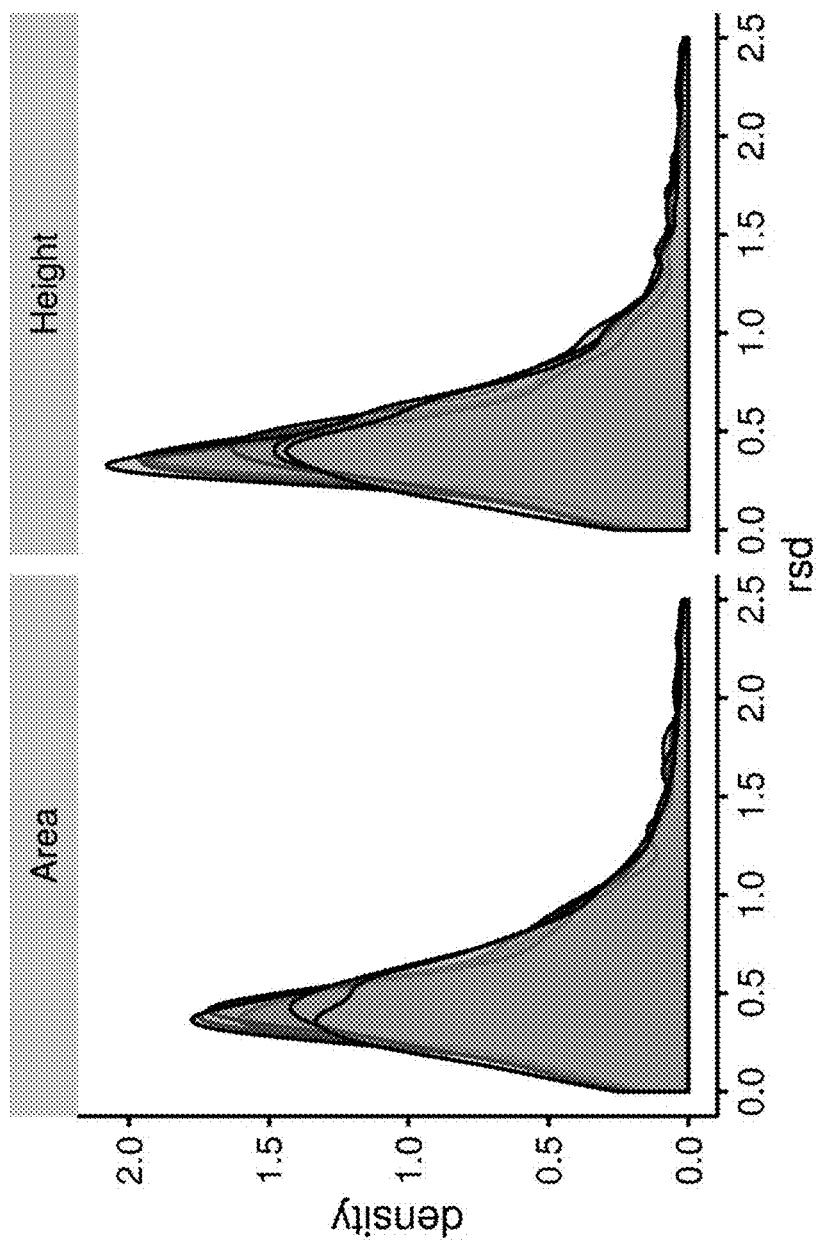
FIG. 7 illustrates the improved relative Standard Deviation of peak heights and areas across normalized scans in a Thermo Orbitrap Fusion Tribrid FTMS spectrum.
Figure 8:
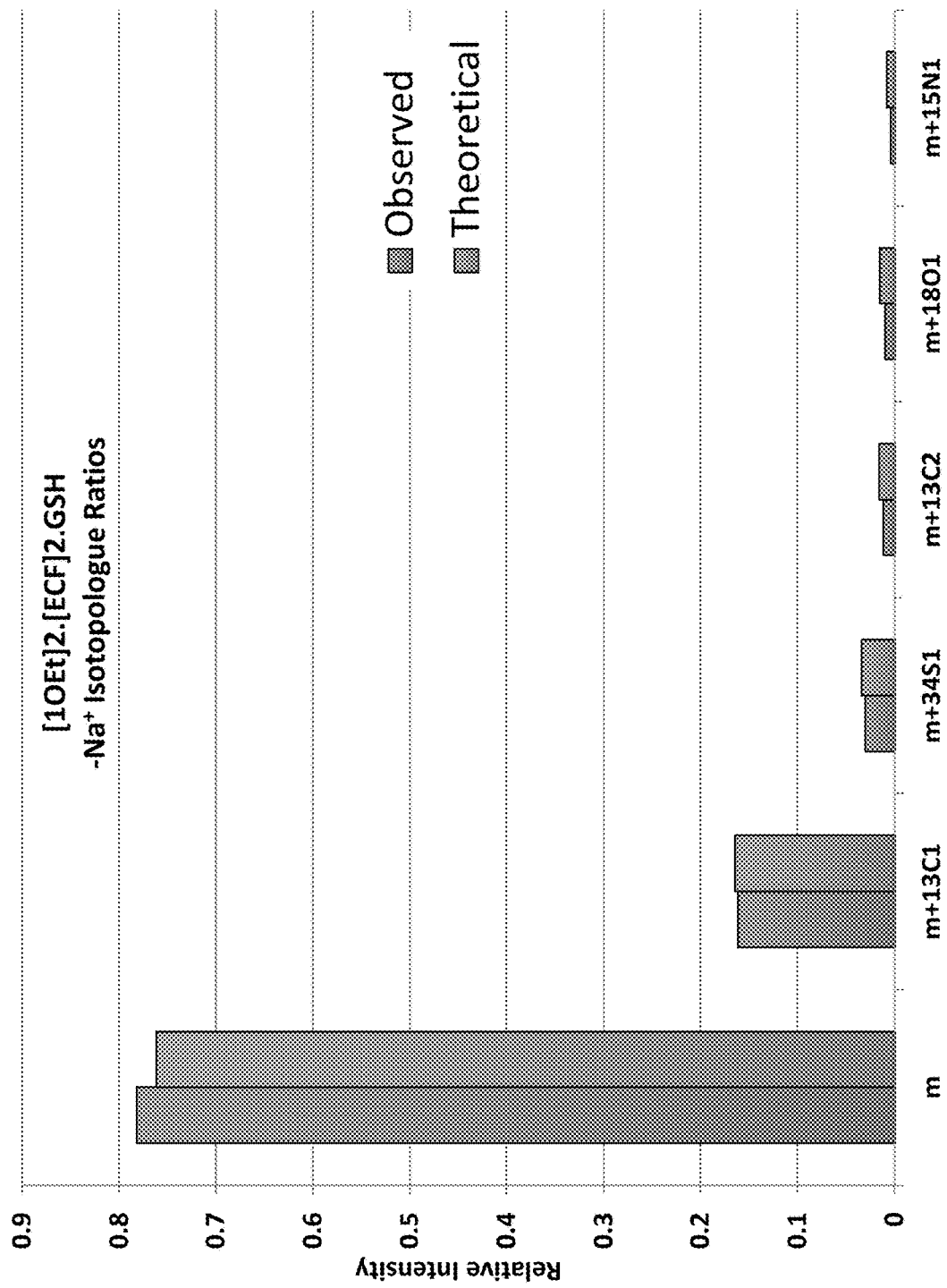
FIG. 8 shows a comparison of observed vs NAP theoretical relative peak heights for a clique of characterized isotopologue peaks.
Figure 9B:
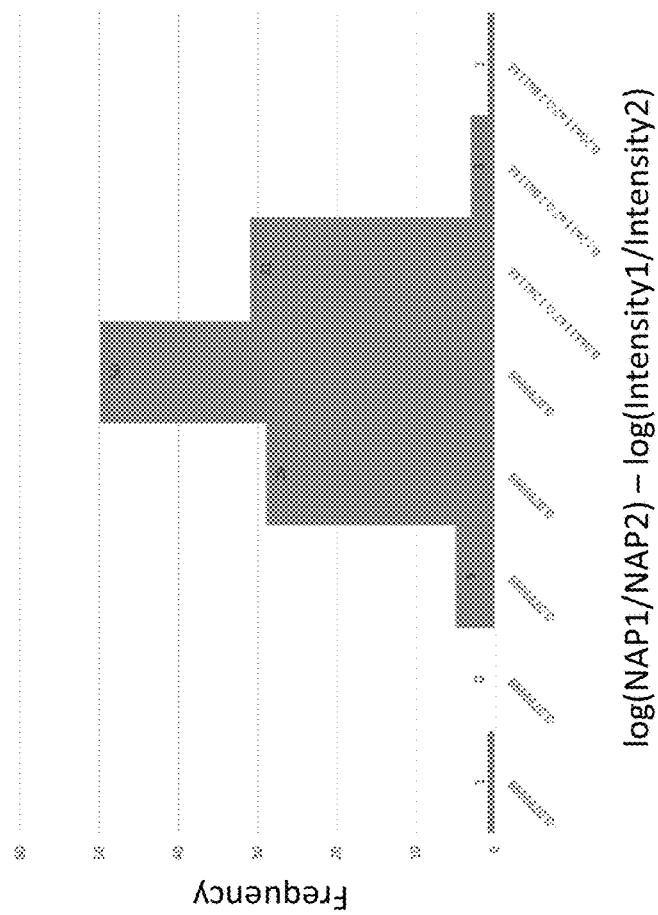
Figure 9A:
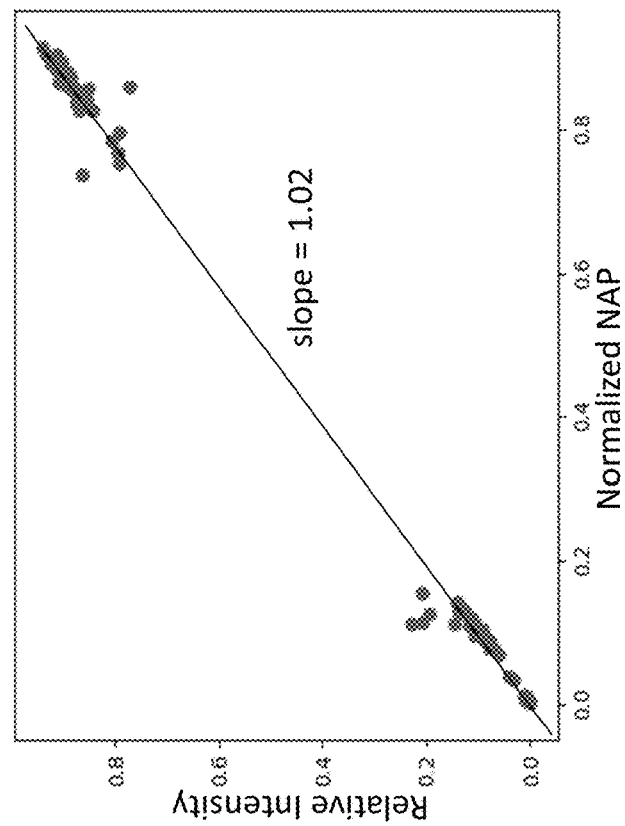

Detected peaks within spectra collected from Fourier transform mass spectrometers have a variety of data quality issues including m/z peak shifting (FIG. 2), inconsistency in peak heights and areas (FIG. 3), and the presence of artefactual peaks. These data quality issues arise from: i) limitations in digital resolution (FIG. 4); ii) problems with scan-level consistency (FIG. 5); and iii) Fourier transform-based artefacts (FIG. 6), and iv) the presence of contaminants. However, standard peak picking methods that average across scans create huge data quality issues. Therefore, an integrated procedure using a combination of new scan-level peak characterization methods along with artefact peak detection methods are required to derive high quality peak characteristics associated with specific isotopologues. Peak characterization at the scan-level is implemented by removing noise peaks per scan, corresponding peaks across scans, and performing normalization of peak heights/areas across scans. The resulting correspondence peaks are used to derive high quality peak heights and areas (FIGS. 7 and 8) while removing many of the high peak density artefacts present but inconsistent at the scan-level. Separate high peak density analyses and contaminant detection will remove or mark the remaining artefactual peaks. A set of contaminant molecules can be based on expected contaminate molecules from the plastics and solvents used in sample preparation including polymers like polyethylene glycol (PEG) and polymer detergents like triton X-100 or derived from quality control samples directly. A difference matrix generated from this list of expected molecules is compared to the difference matrix generated from the peak list derived from a mass spectrum. Rows between the two matrices with a statistically significant number of differences that match are used to assign expected contaminant peaks and derive offsets present in the spectrum.

Component 4. Algorithms that Create Sets of Possible Isotopically-resolved Molecular Formulas by Iteratively Searching the Molecular Formula Caches, Combining with Additional Isotopes and Molecular Fragments, and Statistically Filtering Resulting Isotopically-resolved Molecular Formulas.

Each isotopologue is identified by a peak with a specific mass to charge ratio (m/z ratio) position in the 1D mass spectrum. The peak also has an intensity related to the number of ions physically detected in the mass spectrometer. For each isotopologue, a set of possible isotopically-resolved molecular formulas are calculated within a specified accuracy tolerance using Component 2 to build specific isotopically-resolved molecular formulas and that are then filtered against the NAP from Component 1, a statistical measure of how well the molecular formula matches the m/z ratio (m/z matching probability), and metabolite bonding pattern rules.

Component 5a. Algorithms that Identify Metabolite Cliques of Isotopologues Via the Comparison of Sets of Possible Isotopically-resolved Molecular Formulas from Different Isotopologues that Identify Compatible Element-resolved Molecular Formulas in a Statistically Robust Manner.

A pair of isotopologues are compared via an intersection between their sets of isotopically-resolved molecular formulas that identify compatible isotopically-resolved molecular formulas. Each intersecting pair of complementary isotopiocally-resolved molecular formulas that correspond to the same elemental molecular formula and has equal numbers of labeling isotopes are statistically evaluated using both m/z matching-probabilities from Component 4 and a log ratio of isotopologue peak intensities statistically compared to the log ratio of each isotopically-resolved molecular formula NAP from Component 1 (log-ratio match probability). Each compatible intersecting pair of isotopically-resolved molecular formulas represent evidence for specific elemental molecular formulas (i.e. metabolites) in the mass spectrum. Specific elemental molecular formulas are identified by statically evaluating the sum of compatible intersecting pairs of isotopically-resolved molecular formulas that support the same elemental molecular formula. The resulting analysis identifies a clique of isotopologue peaks associated with a specific elemental molecular formula (i.e. a metabolite isotopologue-offset clique).

Component 5b. Algorithms that Identify Super-cliques of Related Element-resolved Cliques of Isotopologues in a Statistically Robust Manner.

A pair of detected metabolite isotopologue-offset cliques from Component 5a are statistically compared using the matrix of log intensity ratios from Component 5b to identify super-cliques within a mass spectrum with inter-clique differences in both elemental and isotope-specific molecular formulae. These differences reflect additions of known chemoselective tags and/or adducts to specific metabolites represented by the elemental molecular formula of the base clique.

While not all components of this approach are required to obtain useful information, employing all five components can provide for determination of isotopically-resolved molecular formulas of specific isotopologues via the identification of both cliques and super-cliques of isotopologue peaks associated with a specific metabolite or a set of metabolite isomers. Also, this approach is applicable to a directed search of known elemental molecular formulas by building an isotopically-resolved cache (Component 2) for these known elemental molecular formulas. And this approach is applicable to the analysis of tandem mass spectroscopic (MSn) data, where the set of possible isotopically-resolved molecular formulas of specific fragment isotopologues are statistically intersected with the set of possible isotopically-resolved molecular formulas of the parent isotopologue.

Included with this disclosure is an Appendix which includes previous U.S. Provisional Patent Application Ser. No. 62/187,901.

All publications, patents, and patent applications mentioned in this specification are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

REFERENCES

Throughout this document, various references are mentioned. All such references are incorporated herein by reference, including the references set forth in the following list:

1. Moseley, H. N. B., R. M. Higashi, T. W.-M. Fan, and A. N. Lane. Analysis of Non-Steady State Stable Isotope-Resolve Metabolism of UDP-GlcNAc and UDP-GalNAc. in Proceedings of Bioinformatics 2011. 2011. Rome, Italy: SciTePress, Portugal.
2. Django—The Web framework for perfectionists with deadlines. Available from: https://www.djangoproject.com/.
3. Carreer, W. J. and H. N. B. Moseley, Correcting for the effects of natural abundance in stable isotope resolved metabolomics experiments involving multiple simultaneous isotopic labels and ultra-high resolution mass spectrometry Comp Biol Chem, submitted.
4. Moseley, H., Correcting for the effects of natural abundance in stable isotope resolved metabolomics experiments involving ultra-high resolution mass spectrometry. BMC Bioinformatics, 2010. 11: p. 139.
5. Lane, A. N., T. W. Fan, Z. Xie, H. N. Moseley, and R. M. Higashi, Isotopomer analysis of lipid biosynthesis by high resolution mass spectrometry and NMR. Analytica Chimica Acta, 2009. 651(2): p. 201-8.
6. Fan, T. W. M., A. N. Lane, and R. M. Higashi, In vivo and in vitro metabolomic analysis of anaerobic rice coleoptiles revealed unexpected pathways. Russian Journal of Plant Physiology, 2003. 50(6): p. 787-793.
7. Fan, T., J. Bird, E. Brodie, and A. Lane, 13C-Isotopomer-based metabolomics of microbial groups isolated from two forest soils. Metabolomics, 2009. 5(1): p. 108-122.
8. Fan, T. W. and A. N. Lane, NMR-based stable isotope resolved metabolomics in systems biochemistry. Journal of Biomolecular NMR, 2011. 49(3-4): p. 267-80.
9. Lane, A. N., T. W. Fan, and R. M. Higashi, Isotopomer-based metabolomic analysis by NMR and mass spectrometry. Methods Cell Biol, 2008. 84: p. 541-88.

10. Moseley, H., A. Lane, A. Belshoff, R. Higashi, and T. Fan, A novel deconvolution method for modeling UDP-GlcNAc biosynthetic pathways based on 13C mass isotopologue profiles under non steady-state conditions. BMC Biology, 2011. 9(1): p. 37.
11. Tomita, E., A. Tanaka, and H. Takahashi, The worst-case time complexity for generating all maximal cliques and computational experiments. Theoretical Computer Science, 2006. 363(1): p. 28-42.
12. Cazals, F. and C. Karande, A note on the problem of reporting maximal cliques. Theoretical Computer Science, 2008. 407(1-3): p. 564-568.
13. Eppstein, D., M. LOffler, and D. Strash, Listing all maximal cliques in sparse graphs in near-optimal time. Algorithms and Computation, 2010: p. 403-414.
14. Lorkiewicz, P. K., R. M. Higashi, A. N. Lane, and T. W.-M. Fan, High information throughput analysis of nucleotides and their isotopically enriched isotopologues by direct-infusion FTICR-MS. Metabolomics, 2012. in press.
15. Moseley, H. N., Correcting for the effects of natural abundance in stable isotope resolved metabolomics experiments involving ultra-high resolution mass spectrometry. BMC Bioinformatics, 2010. 11: p. 139.
16. Fan, T., M. Kucia, K. Jankowski, R. Higashi, J. Ratajczak, M. Ratajczak, and A. Lane, Rhabdomyosarcoma cells show an energy producing anabolic metabolic phenotype compared with primary myocytes. Molecular Cancer, 2008. 7(1): p. 79.
17. Lane, A. N., T. W. Fan, and R. M. Higashi, Stable isotope-assisted metabolomics in cancer research. IUBMB Life, 2008. 60(2): p. 124-9.
18. Fan, T. W. M., P. Lorkiewicz, K. Sellers, H. N. B. Moseley, R. M. Higashi, and A. N. Lane, Stable isotope-resolved metabolomics and applications for drug development. Pharmacology & Therapeutics, 2012. 133(3): p. 366-391.
19. Fan, T. W.-M. and A. N. Lane, Multi-Dimensional and Multi-Nuclear NMR Assignment Strategies for Metabolomics, in Methodologies for Metabolomics: Experimental Strategies and Techniques, N. Lutz, R. Wevers, and J. Sweedler, Editors. 2012, Cambridge University Press: Cambridge.
20. Cui, Q., I. A. Lewis, A. D. Hegeman, M. E. Anderson, J. Li, C. F. Schulte, W. M. Westler, H. R. Eghbalnia, M. R. Sussman, and J. L. Markley, Metabolite identification via the Madison Metabolomics Consortium Database. Nature Biotechnology, 2008. 26(2): p. 162-164.
21. Vranken, W. F., W. Boucher, T. J. Stevens, R. H. Fogh, A. Pajon, M. Llinas, E. L. Ulrich, J. L. Markley, J. Ionides, and E. D. Laue, The CCPN data model for NMR spectroscopy: development of a software pipeline. Proteins: Structure, Function, and Bioinformatics, 2005. 59(4): p. 687-696.
22. Chignola, F., S. Mari, T. J. Stevens, R. H. Fogh, V. Mannella, W. Boucher, and G. Musco, The CCPN Metabolomics Project: a fast protocol for metabolite identification by 2D-NMR. Bioinformatics, 2011. 27(6): p. 885.
23. Mattingly, S. J., T. Xu, M. H. Nantz, R. M. Higashi, and T. W.-M. Fan, A Carbonyl Capture Approach for Profiling Oxidized Metabolites in Cell Extracts. Metabolomics, 2012: p. In press.
24. Ullmann, J. R., An algorithm for subgraph isomorphism. Journal of the ACM (JACM), 1976. 23(1): p. 31-42.
25. Wishart, D., D. Tzur, C. Knox, R. Eisner, A. Guo, N. Young, D. Cheng, K. Jewell, D. Arndt, and S. Sawhney, HMDB: the human metabolome database. Nucleic Acids Research, 2007. 35(Database issue): p. D521.
26. Kanehisa, M., S. Goto, M. Hattori, K. Aoki-Kinoshita, M. Itoh, S. Kawashima, T. Katayama, M. Araki, and M. Hirakawa, From genomics to chemical genomics: new developments in KEGG. Nucleic Acids Research, 2006. 34(Database Issue): p. D354.
27. Rogers, D. J. and T. T. Tanimoto, A computer program for classifying plants. Science, 1960. 132(3434): p. 1115.
28. Watanabe, K., E. Yasugi, and M. Oshima, How to Search the Glycolipid data in "LIPID. Trends in Glycoscience and Glycotechnology, 2000. 12(65): p. 175-184.
29. Redestig, H., M. Kusano, A. Fukushima, F. Matsuda, K. Saito, and M. Arita, Consolidating metabolite identifiers to enable contextual and multi-platform metabolomics data analysis. BMC bioinformatics, 2010. 11(1): p. 214.
30. Pence, H. E. and A. Williams, ChemSpider: an online chemical information resource. Journal of Chemical Education, 2010.
31. Ogata, H., S. Goto, K. Sato, W. Fujibuchi, H. Bono, and M. Kanehisa, KEGG: Kyoto Encyclopedia of Genes and Genomes. Nucleic Acids Res, 1999. 27(1): p. 29-34.
32. Cline, M. S., M. Smoot, E. Cerami, A. Kuchinsky, N. Landys, C. Workman, R. Christmas, I. Avila-Campilo, M. Creech, B. Gross, K. Hanspers, R. Isserlin, R. Kelley, S. Killcoyne, S. Lotia, S. Maere, J. Morris, K. Ono, V. Pavlovic, A. R. Pico, A. Vailaya, P. L. Wang, A. Adler, B. R. Conklin, L. Hood, M. Kuiper, C. Sander, I. Schmulevich, B. Schwikowski, G. J. Warner, T. Ideker, and G. D. Bader, Integration of biological networks and gene expression data using Cytoscape. Nature Protocols, 2007. 2(10): p. 2366-2382.
33. Shannon, P., A. Markiel, O. Ozier, N. S. Baliga, J. T. Wang, D. Ramage, N. Amin, B. Schwikowski, and T. Ideker, Cytoscape: A software environment for integrated models of biomolecular interaction networks. Genome Research, 2003. 13(11): p. 2498-2504.
34. Bolker, B. M., M. E. Brooks, C. J. Clark, S. W. Geange, J. R. Poulsen, M. H. H. Stevens, and J. S. S. White, Generalized linear mixed models: a practical guide for ecology and evolution. Trends in Ecology & Evolution, 2009. 24(3): p. 127-135.
35. Breslow, N. and N. Day, Statistical Methods in Cancer Research: Volume 1—The Analysis of Case-Control Studies. Vol. 32. 1980, Lyon: IARC Scientific Publications
36. Agresti, A., Categorical data analysis. 2nd. ed. 2002, New York: Wiley and Sons.
37. Bonacich, P., Factoring and weighting approaches to status scores and clique identification. Journal of Mathematical Sociology, 1972. 2(1): p. 113-120.
38. Kose, F., W. Weckwerth, T. Linke, and 0. Fiehn, Visualizing plant metabolomic correlation networks using clique-metabolite matrices. Bioinformatics, 2001. 17(12): p. 1198-1208.
39. Bqnjamini, Y. and Y. Hochberg, Controlling the false discovery rate: A practical and powerful approach to multiple testing. J. Roy. Statist. Soc. B, 1995. 57: p. 289-300.
40. Pounds, S. and S. N. Rai, Assumption adequacy averaging as a concept for developing more robust methods for differential gene expression analysis. Computational Statistics & Data Analysis, 2009. 53(5): p. 1604-1612.
41. Karakach, T. K., P. D. Wentzell, and J. A. Walter, Characterization of the measurement error structure in ID I H NMR data for metabolomics studies. Analytica Chimica Acta, 2009. 636(2): p. 163-174.

42. Boyle, E. I., S. A. Weng, J. Gollub, H. Jin, D. Botstein, J. M. Cherry, and G. Sherlock, GO:: TermFinder—open source software for accessing Gene Ontology information and finding significantly enriched Gene Ontology terms associated with a list of genes. Bioinformatics, 2004. 20(18): p. 3710-3715.

43. Rosner, B., Fundamentals of Biostatistics. sixth ed. 2006, Belmont Calif.: Thomson.

44. Agrawal, R., J. Gehrke, D. Gunopulos, and P. Raghavan, Automatic subspace clustering of high dimensional data. Data Mining and Knowledge Discovery, 2005. 11(1): p. 5-33.

45. Bylesjo, M., M. Rantalainen, 0. Cloarec, J. K. Nicholson, E. Holmes, and J. Trygg, OPLS discriminant analysis: combining the strengths of PLS-DA and SIMCA classification. Journal of Chemometrics, 2006. 20(8-10): p. 341-351.

46. Rajaram, S. and Y. Oono, NeatMap-non-clustering heat map alternatives in R. BMC bioinformatics, 2010. 11(1): p. 45.

47. Wold, S., J. Trygg, A. Berglund, and H. Antti, Some recent developments in PLS modeling. Chemometrics and Intelligent Laboratory Systems, 2001. 58(2): p. 131-150.

48. Trygg, J., E. Holmes, and T. Lundstedt, Chemometrics in metabonomics. Journal of Proteome Research, 2007. 6(2): p. 469-479.

49. Breiman, L., Random forests. Machine learning, 2001. 45(1): p. 5-32.

50. Liaw, A. and M. Wiener, Classification and Regression by random Forest. R news, 2002. 2(3): p. 18-22.

51. Lee, Y. and C. Lee, Classification of multiple cancer types by multicategory support vector machines using gene expression data. Bioinformatics, 2003. 19(9): p. 1132.

52. Dimitriadou, B., Hornik, K., Leisch, F., Meyer, D., & Weingessel, A., "e1071: Misc Functions of the Department of Statistics (e1071), TU Wien, Version 1.5-11. 2005.

53. Bylesjo, M., M. Rantalainen, J. Nicholson, E. Holmes, and J. Trygg, K-OPLS package: Kernel-based orthogonal projections to latent structures for prediction and interpretation in feature space. BMC bioinformatics, 2008. 9(1): p. 106.

54. Yang, X., K. Su, M. D. Roos, 0. Chang, A. J. Paterson, and J. E. Kudlow, 0-linkage of N-acetylglucosamine to Spl activation domain inhibits its transcriptional capability. Proc Natl Acad Sci USA, 2001. 98(12): p. 6611-6.

55. Taylor, R. P., G. J. Parker, M. W. Hazel, Y. Soesanto, W. Fuller, M. J. Yazzie, and D. A. McClain, Glucose deprivation stimulates O-GlcNAc modification of proteins through up-regulation of 0-linked N-acetylglucosaminyl-transferase. J Biol Chem, 2008. 283(10): p. 6050-7.

56. Warner, J. B., C. Thalhauser, K. Tao, and G. G. Sahagian, Role of N-linked oligosaccharide flexibility in mannose phosphorylation of lysosomal enzyme cathepsin L. J Biol Chem, 2002. 277(44): p. 41897-905.

57. Selivanov, V., P. Vizan, F. Mollinedo, T. Fan, P. Lee, and M. Cascante, Edelfosine-induced metabolic changes in cancer cells that precede the overproduction of reactive oxygen species and apoptosis. BMC Systems Biology, 2010. 4(1): p. 135.

58. Wahl, S. A., K. MTh, and W. Wiechert, 13C labeling experiments at metabolic nonstationary conditions: an exploratory study. BMC bioinformatics, 2008. 9(1): p. 152.

59. Selivanov, V. A., S. Marin, P. W. N. Lee, and M. Cascante, Software for dynamic analysis of tracer-based metabolomic data: estimation of metabolic fluxes and their statistical analysis. Bioinformatics, 2006. 22(22): p. 2806-2812.

60. Arita, M., In silico atomic tracing by substrate-product relationships in *Escherichia coli* intermediary metabolism. Genome Research, 2003. 13(11): p. 2455-2466.

61. Caspi, R., H. Foerster, C. A. Fulcher, P. Kaipa, M. Krummenacker, M. Latendresse, S. Paley, S. Y. Rhee, A. G. Shearer, and C. Tissier, The MetaCyc database of metabolic pathways and enzymes and the BioCyc collection of pathway/genome databases. Nucleic acids research, 2008. 36(suppl 1): p. D623-D631.

62. Krieger, C. J., P. Zhang, L. A. Mueller, A. Wang, S. Paley, M. Arnaud, J. Pick, S. Y. Rhee, and P. D. Karp, MetaCyc: a multiorganism database of metabolic pathways and enzymes. Nucleic acids research, 2004. 32(suppl 1): p. D438-D442.

63. Joshi-Tope, G., M. Gillespie, I. Vastrik, P. D'Eustachio, E. Schmidt, B. de Bono, B. Jassal, G. Gopinath, G. Wu, and L. Matthews, Reactome: a knowledgebase of biological pathways. Nucleic Acids Research, 2005. 33(Database Issue): p. D428.

64. Matthews, L., G. Gopinath, M. Gillespie, M. Caudy, D. Croft, B. De Bono, P. Garapati, J. Hemish, H. Hermjakob, and B. Jassal, Reactome knowledgebase of human biological pathways and processes. Nucleic Acids Research, 2009. 37(Database issue): p. D619.

65. Apweiler, R., A. Bairoch, C. H. Wu, W. C. Barker, B. Boeckmann, S. Ferro, E. Gasteiger, H. Huang, R. Lopez, and M. Magrane, UniProt: the universal protein knowledgebase. Nucleic acids research, 2004. 32(suppl 1): p. D115-D119.

66. Bairoch, A., R. Apweiler, C. H. Wu, W. C. Barker, B. Boeckmann, S. Ferro, E. Gasteiger, H. Huang, R. Lopez, and M. Magrane, The universal protein resource (UniProt). Nucleic acids research, 2005. 33(suppl 1): p. D154-D159.

67. Baker, W., A. Van Den Broek, E. Camon, P. Hingamp, P. Sterk, G. Stoesser, and M. A. Tuli, The EMBL nucleotide sequence database. Nucleic acids research, 2000. 28(1): p. 19-23.

68. Kulikova, T., R. Akhtar, P. Aldebert, N. Althorpe, M. Andersson, A. Baldwin, K. Bates, S. Bhattacharyya, L. Bower, and P. Browne, EMBL nucleotide sequence database in 2006. Nucleic acids research, 2007. 35(suppl 1): p. D16-D20.

69. Kulikova, T., P. Aldebert, N. Althorpe, W. Baker, K. Bates, P. Browne, A. Van Den Broek, G. Cochrane, K. Duggan, and R. Eberhardt, The EMBL nucleotide sequence database. Nucleic acids research, 2004. 32(suppl 1): p. D27-D30.

70. Pagel, P., S. Kovac, M. Oesterheld, B. Brauner, I. Dunger-Kaltenbach, G. Frishman, C. Montrone, P. Mark, V. StUmpflen, and H. W. Mewes, The MIPS mammalian protein-protein interaction database. Bioinformatics, 2005. 21(6): p. 832-834.

71. Finn, R. D., M. Marshall, and A. Bateman, iPfam: visualization of protein-protein interactions in PDB at domain and amino acid resolutions. Bioinformatics, 2005. 21(3): p. 410-412.

72. Davis, F. P. and A. Sali, PIBASE: a comprehensive database of structurally defined protein interfaces. Bioinformatics, 2005. 21(9): p. 1901-1907.

73. Kuang, X., J. G. Han, N. Zhao, B. Pang, C. R. Shyu, and D. Korkin, DOMMINO: a database of macromolecular interactions. Nucleic acids research, 2012. 40(D1): p. D501-D506.

74. Aloy, P. and R. B. Russell, InterPreTS: protein interaction prediction through tertiary structure. Bioinformatics, 2003. 19(1): p. 161-162.
75. Qi, Y., Z. Bar-Joseph, and J. Klein-Seetharaman, Evaluation of different biological data and computational classification methods for use in protein interaction prediction. Proteins: Structure, Function, and Bioinformatics, 2006. 63(3): p. 490-500.
76. Pazos, F. and A. Valencia, Similarity of phylogenetic trees as indicator of protein-protein interaction. Protein engineering, 2001. 14(9): p. 609-614.
77. Jansen, R., H. Yu, D. Greenbaum, Y. Kluger, N. J. Krogan, S. Chung, A. Emili, M. Snyder, J. F. Greenblatt, and M. Gerstein, A Bayesian networks approach for predicting protein-protein interactions from genomic data. Science, 2003. 302(5644): p. 449-453.
78. Bradford, J. R. and D. R. Westhead, Improved prediction of protein-protein binding sites using a support vector machines approach. Bioinformatics, 2005. 21(8): p. 1487-1494.
79. Shen, J., J. Zhang, X. Luo, W. Zhu, K. Yu, K. Chen, Y. Li, and H. Jiang, Predicting protein-protein interactions based only on sequences information. Proceedings of the National Academy of Sciences, 2007. 104(11): p. 4337.
80. Ashburner, M., C. A. Ball, J. A. Blake, D. Botstein, H. Butler, J. M. Cherry, A. P. Davis, K. Dolinski, S. S. Dwight, and J. T. Eppig, Gene Ontology: tool for the unification of biology. Nature genetics, 2000. 25(1): p. 25.
81. Mungall, C. J., M. Bada, T. Z. Berardini, J. Deegan, A. Ireland, M. A. Harris, D. P. Hill, and J. Lomax, Cross-product extensions of the Gene Ontology. Journal of biomedical informatics, 2011. 44(1): p. 80-86.
82. Eppstein, D., Finding the k shortest paths. SIAM J. Comput., 1998. 28(2): p. 652-673.
83. Hershberger, J., M. Maxel, and S. Suri, Finding the k shortest simple paths: A new algorithm and its implementation. ACM Transactions on Algorithms (TALG), 2007. 3(4): p. 45.
84. Akaike, H., A new look at the statistical model identification. IEEE transactions on automatic control, 1974. 19(6): p. 716-723.
85. Fan, T., L. Bandura, R. Higashi, and A. Lane, Metabolomics-edited transcriptomics analysis of Se anticancer action in human lung cancer cells. Metabolomics Journal, 2005. 1(4): p. 325-339
86. Fan, T. W.-M., ed. Metabolomics-Edited Transcriptomics Analysis (Meta). Comprehensive Toxicology, ed. C. A. McQueen. Vol. 2. 2010, Academic Press: Oxford. 685-706.
87. Sherry, S., M. H. Ward, M. Kholodov, J. Baker, L. Phan, E. Smigielski, and K. Sirotkin, dbSNP: the NCBI database of genetic variation. Nucleic acids research, 2001. 29(1): p. 308-311.
88. Edgar, R., M. Domrachev, and A. E. Lash, Gene Expression Omnibus: NCBI gene expression and hybridization array data repository. Nucleic acids research, 2002. 30(1): p. 207-210.
89. Barrett, T., D. B. Troup, S. E. Wilhite, P. Ledoux, C. Evangelista, I. F. Kim, M. Tomashevsky, K. A. Marshall, K. H. Phillippy, P. M. Sherman, R. N. Muertter, M. Holko, O. Ayanbule, A. Yefanov, and A. Soboleva, NCBI GEO: archive for functional genomics data sets—10 years on. Nucleic Acids Res, 2011. 39(Database issue): p. D1005-10.
90. Jones, P., R. G. Cote, S. Y. Cho, S. Klie, L. Martens, A. F. Quinn, D. Thorneycroft, and H. Hermjakob, PRIDE: new developments and new datasets. Nucleic acids research, 2008. 36(suppl 1): p. D878-D883.
91. Martens, L., H. Hermjakob, P. Jones, M. Adamski, C. Taylor, K. Gevaert, J. Vandekerckhove, and R. Apweiler, PRIDE: the proteomics identifications database. Proteomics, 2005. 5(13): p. 3537-3545.
92. Diggle P J, Heagerty P J, Liang K Y, and Z. S L., Analysis of Longitudinal Data. Vol. 2. 2002, Oxford: Oxford University Press.
93. Rai, S. N., H. E. Ray, X. Yuan, J. Pan, T. Hamid, and S. D. Prabhu, Statistical Analysis of Repeated MicroRNA High-Throughput Data with Application to Human Heart Failure: A Methodology Review. Open Accesses Medical Statistics Journal, 2012. in press.
94. Davies, R. L. a. M., H. N. B., Student Roots: Square root algorithm in Forth. Forth Dimensions, 1987. 8: p. 8-9.
95. Moseley, H., Scaffolded Explicit Revision as a Practical Framework to Promote Effective Student Effort in Content-Rich Science Courses. J College Sci Teach, submitted.
96. Borg, M. O., P. M. Mason, and S. L. Shapiro, The case of effort variables in student performance. Journal of Economic Education, 1989: p. 308-313.
97. Williams, R. L. and L. Clark, College students' ratings of student effort, student ability and teacher input as correlates of student performance on multiple-choice exams. Educational Research, 2004. 46(3): p. 229-239.
98. Ericsson, K. A. and P. Ward, Capturing the naturally occurring superior performance of experts in the laboratory. Current Directions in Psychological Science, 2007. 16(6): p. 346.
99. Pintrich, P. R. and E. V. De Groot, Motivational and self-regulated learning components of classroom academic performance. Journal of Educational Psychology, 1990. 82(1): p. 33.
100. Elliot, A. J., H. A. McGregor, and S. Gable, Achievement goals, study strategies, and exam performance: A mediational analysis. Journal of Educational Psychology, 1999. 91(3): p. 549.
101. Arum, R. and J. Roksa, Academically adrift: Limited learning on college campuses. 2011: University of Chicago Press.
102. Babcock, P. and M. Marks, The falling time cost of college: Evidence from half a century of time use data. Review of Economics and Statistics, 2011. 93(2): p. 468-478.
103. Black, P. and D. Wiliam, Developing the theory of formative assessment. Educational Assessment, Evaluation and Accountability, 2009. 21(1): p. 5-31.
104. Black, P. and D. Wiliam, Assessment and classroom learning. Assessment in education, 1998. 5(1): p. 7-74.
105. Dunn, K. E. and S. W. Mulvenon, A critical review of research on formative assessment: The limited scientific evidence of the impact of formative assessment in education. Practical Assessment, Research & Evaluation, 2009. 14(7): p. 1-11.
106. Schamber, J. F. and S. L. Mahoney, Assessing and improving the quality of group critical thinking exhibited in the final projects of collaborative learning groups. The Journal of General Education, 2006. 55(2): p. 103-137.
107. Bean, J., Engaging Ideas: The Professor's Guide to Integrating Writing, Critical Thinking and Active Learning in the Classroom. 1996, Jossey-Bass.
108. Clement, J., Model based learning as a key research area for science education. International Journal of Science Education, 2000. 22(9): p. 1041-1053.

109. Fitzgerald, J., Research on revision in writing. Review of Educational Research, 1987. 57(4): p. 481.
110. Fitzgerald, J. and L. R. Markham, Teaching children about revision in writing. Cognition and Instruction, 1987. 4(1): p. 3-24.
111. Lee, A., Composing critical pedagogies: Teaching writing as revision. 2000: Natl Council of Teachers.
112. Hillocks Jr, G., Synthesis of research on teaching writing. Educational Leadership, 1987. 44(8): p. 71-82.
113. Hillocks Jr, G., The interaction of instruction, teacher comment, and revision in teaching the composing process. Research in the Teaching of English, 1982: p. 261-278.
114. Barab, S. and K. Squire, Design-based research: Putting a stake in the ground. The journal of the learning sciences, 2004. 13(1): p. 1-14.
115. Sandoval, W. A. and P. Bell, Design-based research methods for studying learning in context: Introduction. Educational psychologist, 2004. 39(4): p. 199-201.
116. Brown, A. L., Design experiments: Theoretical and methodological challenges in creating complex interventions in classroom settings. The journal of the learning sciences, 1992. 2(2): p. 141-178.
117. Collins, A., Towards a Design Science in Education. In E. Scanlon & T. O'Shea (eds) New Directions in Educational Technology. 1992, Springer-Verlag: New York.
118. Paul, R. and L. Elder, The miniature guide to critical thinking: Concepts and tools. Vol. 2. 2001: Foundation for Critical Thinking.
119. Mayer, R. E., Multimedia learning: Are we asking the right questions? Educational psychologist, 1997. 32(1): p. 1-19.
120. Prince, M., Does active learning work? A review of the research. JOURNAL OF ENGINEERING EDUCATION-WASHINGTON-, 2004. 93: p. 223-232.
121. Handelsman, J., S. Miller, and C. Pfund, Scientific teaching. 2006: WH Freeman & Co.
122. Nosich, G. M., Learning to think things through: A guide to critical thinking across the curriculum. 2005: Prentice Hall.
123. Slavin, R. E., Research on cooperative learning and achievement: What we know, what we need to know. Contemporary educational psychology, 1996. 21: p. 43-69.
124. Karpicke, J. D. and H. L. Roediger, The critical importance of retrieval for learning. science, 2008. 319 (5865): p. 966.
125. Smith III, J. P., A. A. diSessa, and J. Roschelle, Misconceptions reconceived: A constructivist analysis of knowledge in transition. The journal of the learning sciences, 1994. 3(2): p. 115-163.
126. Anderson, L. W., D. R. Krathwohl, P. W. Airasian, K. A. Cruikshank, R. E. Mayer, P. Pintrich, J. Raths, and M. Wittrock, A taxonomy for learning, teaching, and assessing: A revision of Bloom's taxonomy of educational objectives. 2000: Allyn & Bacon.
127. Ames, C., Classrooms: Goals, structures, and student motivation. Journal of educational psychology, 1992. 84(3): p. 261.
128. Schunk, D. H. and B. J. Zimmerman, Self-regulation of learning and performance: Issues and educational applications. 1994: Lawrence Erlbaum.
129. Bangert-Drowns, R. L., J. A. Kulik, and C. L. C. Kulik, Effects of frequent classroom testing. The Journal of Educational Research, 1991. 85: p. 89-99.
130. lhaka, R. and R. Gentleman, R: a language for data analysis and graphics. Journal of computational and graphical statistics, 1996: p. 299-314.
131. Faraway, J. J., Practical Regression and ANOVA using R. 2002, Citeseer.
132. Wherry, R. J., A new formula for predicting the shrinkage of the coefficient of multiple correlation. The annals of mathematical statistics, 1931. 2(4): p. 440-457.
133. Yin, P. and X. Fan, Estimating $R^2$ Shrinkage in Multiple Regression: A Comparison of Different Analytical Methods. The Journal of Experimental Education, 2001. 69(2): p. 203-224.
134. Cohen, J., Statistical power analysis for the behavioral sciences. 1988: Lawrence Erlbaum.
135. Maxwell, S. E., Sample size and multiple regression analysis. Psychological Methods, 2000. 5(4): p. 434.
136. Huberty, C. J., A history of effect size indices. Educational and Psychological Measurement, 2002. 62(2): p. 227.
137. Champely, S. and M. S. Champely, Package 'pwr'. 2009.
138. Blackwell, L. S., K. H. Trzesniewski, and C. S. Dweck, Implicit theories of intelligence predict achievement across an adolescent transition: A longitudinal study and an intervention. Child Development, 2007. 78(1): p. 246-263.
139. Dweck, C. S., The perils and promises of praise. Best of Educational Leadership, 2008. 65: p. 34-39.
140. U.S. Pat. No. 8,510,054 for "Intracellular Metabolic Flux Analysis Method Using Substrate Labeled with Isotope" to Iwakani.
141. U.S. Pat. No. 8,481,478 for "Method For Automated, Large-Scale Measurement of the Molecular Flux Rates of The Proteome or the Organeome Using Mass Spectrometry" to Hellerstein.
142. U.S. Pat. No. 8,420,406 for "Method for Analysing Metabolites" to Lüdemann, et al.
143. U.S. Pat. No. 8,129,335 for "Method For Automated, Large-Scale Measurement of the Molecular Flux Rates of the Proteome or the Organeome Using Mass Spectrometry" to Hellerstein.
144. U.S. Pat. No. 8,116,983 for "Device for Quantitative Analysis of a Drug or Metabolite Profile" to Ramsay, et al.
145. U.S. Pat. No. 7,402,437 for "Method and Device for Analyzing the Intracellular Chemical State of Living Cells by Nuclear Magnetic Resonance" to Gonzalez, et al.
146. U.S. Pat. No. 6,764,817 for "Method for Conducting Metabolic Analyses" to Schneider
147. US 2014/0212872 for "Identity Elucidation of Unknown Metabolites" to Milburn, et al.
148. US 2008/0081375 for "Metabolite Detection Using Magnetic Resonance" to Tesiram.
149. US 2006/0094057 for "Method For Automated, Large-Scale Measurement of the Molecular Flux Rates of the Proteome or the Organeome Using Mass Spectrometry" to Hellerstein.
150. US 2005/0175982 for "Intracellular Metabolic Flux Analysis Method using Substrate Labeled with Isotope" to Itwatani, et al.
151. US 2005/0281745 for "Stable Isotope Based Dynamic Metabolic Profiling of Living Organisims for Characterization of Metabolic Diseases, Drug Testing and Drug Development" to Lee, et al.

152. US 2003/0180800 for "Stable Isotope Based Dynamic Metabolic Profiling of Living Organisims for Characterization of Metabolic Diseases, Drug Testing and Drug Development" to Lee, et al.
153. US 2003/0180710 for "Method of Enhancing the Efficiency of a Pharmaceutical Business" to Lee, et al.
154. WO-2013/170099 for "Calibration of Haptic Feedback Systems for Input Devices" to O'Day, et al.
155. JP-2006337176 for Determination Method of Metabolite ODA
156. Birkemeyer, et al. Metabolome analysis: the potential of in vivo labeling with stable isotopes for metabolite profiling Trends in Biotechnology, 2005, 23(1): 29-33
157. Browne, et al. Performance of human mass balance/metabolite identification studies using stable isotope (13C, 15N) labeling and continuous-flow isotope-ratio mass spectrometry as an alternative to radioactive labeling methods. J Clin Pharmacol. 1993 March; 33(3):246-52.
158. Creek, et al. Stable Isotope-Assisted Metabolomics for Network-Wide Metabolic Pathway Elucidation Bioanalysis (2013) 5(15), 1807-1810
159. Dunn, et al. Mass appeal: metabolite identification in mass spectrometry-focused untargeted metabolomics Metabolomics, 2012
160. Gowda, et al. Quantitative analysis of blood plasma metabolites using isotope enhanced NMR methods Anal Chem. 2010 Nov. 1; 82(21):8983-90
161. Kumari, et al. Applying in-silico retention index and mass spectra matching for identification of unknown metabolites in accurate mass GC-TOF mass spectrometry. Anal Chem. 2011 Aug. 1; 83(15):5895-902
162. Nakayama, et al. Novel Strategy for Non-Targeted Isotope-Assisted Metabolomics by Means of Metabolic Turnover and Multivariate Analysis Metabolites, 2014; 4: 722-739
163. Sano, et al. A new technique for the detection of metabolites labelled by the isotope 13C using mass fragmentography. Biomed Mass Spectrom. 1976 February; 3(1): 1-3
164. Sinha, et al. Algorithm for locating analytes of interest based on mass spectral similarity in GC x GC-TOF-MS data: analysis of metabolites in human infant urine. J Chromatogr A. 2004 Nov. 26; 1058(1-2):209-15
165. VandenHeuvel, W J. Drug metabolite identification: stable isotope methods. J Clin Pharmacol. 1986 July-August; 26(6):427-34.
166. Yan, et al. Rapid detection and characterization of minor reactive metabolites using stable-isotope trapping in combination with tandem mass spectrometry. Rapid Commun Mass Spectrom. 2005; 19(22):3322-30
167. Yang, et al. In vitro stable isotope labeling for discovery of novel metabolites by liquid chromatography-mass spectrometry: Confirmation of gamma-tocopherol metabolism in human A549 cell. J Chromatogr A. 2010 Jan. 29; 1217(5):667-75. doi: 10.1016/j.chroma.2009.12.002. Epub 2009 Dec. 4
168. Yang, et al. Simultaneous quantification of metabolites involved in central carbon and energy metabolism using reversed-phase liquid chromatography-mass spectrometry and in vitro 13C labeling. Anal Chem. 2008 Dec. 15; 80(24):9508-16
169. You, et al. Application of Stable Isotope-Assisted Metabolomics for Cell Metabolism Studies Metabolites, 2014, 4: 142-165
170. Metabolite Identification in Synechococcus sp. PCC 7002 Using Untargeted Stable Isotope Assisted Metabolite Profiling; Richard Baran, Benjamin P. Bowen, Nicholas J. Bouskill, Eoin L. Brodie, Steven M. Yannone, and Trent R. Northen; Analytical Chemistry 2010 82 (21), 9034-9042
171. Automated LC-HRMS(/MS) Approach for the Annotation of Fragment Ions Derived from Stable Isotope Labeling-Assisted Untargeted Metabolomics; Nora K. N. Neumann†, Sylvia M. Lehner, Bernhard Kluger, Christoph Bueschl, Karoline Sedelmaier†, Marc Lemmens, Rudolf Krska, and Rainer Schuhmacher; Anal. Chem., 2014, 86 (15), pp 7320-7327.
172. Drug Metabolism Handbook: Concepts and Applications; By Ala F. Nassar; 2009
173. Identification of unknown metabolites: structure generation and candidate rejection http://analyticalbiosciences.leidenuniv.nl/research/projects/identification-of-unknown -metabolites-structure-generation-and-candidate-rejection
174. Dealing with the Unknown: Metabolomics and Metabolite Atlases; Benjamin P. Bowen and Trent R. Northen; Journal of the American Society for Mass Spectrometry; Volume 21, Issue 9, September 2010, Pages 1471-1476
175. MetaSIRMS™ Stable Isotope Ratio Metabolomics http://www.targetdiscovery.com/~tdidocs/MetaSIRMS%20Brief_RevA.pdf
176. Stable isotope labeled metabolomics improves identification of novel metabolites and pathways; Darren J Creek; Future Science; August 2013, Vol. 5, No. 15, Pages 1807-1810
177. Mapping Microbial Metabolism http://biinformatics.ai.sri.com/ptools13/slides/Wed/baran.pdf
178. Development of isotags for NMR based metabolite profiling and applications; Fariba Tayyari, dissertation; Purdue University

What is claimed is:

1. A method for mass spectrometry data analysis for identification of a specific elemental molecular formula (EMF) for an unknown compound, the method comprising:
calculating a natural abundance probability (NAP) of a given isotopologue for isotopes of a predetermined mass and elemental boundary for non-labeling elements of an unknown compound based on chemical norms for possible structures;
creating caches of non-ionized molecular fragments for a subset of isotopes identified using the NAP values for isotopologues above a NAP cutoff which is based on an expected detection dynamic range for a specific mass spectrometry instrument;
sorting the caches of molecular fragments into a requisite cache data structure, to be searched;
characterizing peaks from a raw mass spectrum composed of multiple scans without spectral nor regional averaging for an unknown compound and separating sample-specific peaks from various spectral artefacts seen in ultra-high resolution Fourier transform mass spectra;
creating sets of possible isotope-resolved molecular formulae (IMF) by iteratively searching the molecular fragment caches and combining with additional isotopes and then statistically filtering the results based on NAP and mass-to-charge (m/z) matching probabilities; and
identifying an unknown compound and its corresponding EMF from statistically-significant cliques of isotopologues with compatible IMFs.

2. The method of claim 1, wherein calculating a natural abundance probability (NAP) of a given isotopologue for isotopes of non-labeling elements of an unknown compound comprises applying the equation:

$$P_E(k_1, k_2, \ldots, k_m) = \binom{E_{Max}}{k_1, k_2, \ldots, k_m} \prod_{x=1}^{m} NA_{E_{lx}}^{k_x}$$

$$NAP = \prod_{j=1}^{n} P_{Ej}$$

where, in an instance a specific isotope(s) comes from a labeling source, probability ($P_E$) is omitted from the calculation.

3. The method of claim 1, wherein creating caches of non-ionized molecular fragments for a subset of isotopes identified using the NAP, and sorting the caches of molecular fragments into the requisite cache data structure, comprises:
enumerating molecular fragments for a given set of isotopes within a mass specified mass range,
calculating partial NAP for each molecular fragments,
filtering molecular fragments based on a given NAP cutoff,
sorting molecular fragments by mass, and
generating a binary or b-tree searchable molecular fragment cache.

4. The method of claim 1, wherein characterizing peaks from the raw mass spectrum and separating sample-specific peaks from various spectral artefacts seen in ultra-high resolution Fourier transform mass spectra comprises:
removing noise peaks from multiple mass spectrometry scans of the unknown compound,
corresponding peaks across the multiple scans after noise peaks removed, and
performing normalization of peak heights/areas across scans.

5. The method of claim 4, wherein identifying a metabolite and its corresponding EMF from statistically-significant cliques of isotopologues with compatible IMFs comprises:
identifying a nonempty intersection between sets of possible EMFs identify from possible IMFs;
statistically evaluating using both the m/z matching probabilities calculated, for each complementary pair of isotopologues from one of the specific respective EMF cliques and statistically comparing a log ratio of isotopologue intensities to a log ratio of each of the IMF NAP,
wherein the isotopologue intensities used in the ratios are derived from associated
characterized peaks; and
identifying specific EMF cliques identified by statically evaluating the sum of complementary pair probabilities/likelihoods.

6. The method of claim 1, wherein creating sets of possible isotope-resolved molecular formulae (IMF) by iteratively searching the molecular fragment caches and combining with additional isotopes and then statistically filtering the results based on NAP and mass-to-charge (m/z) matching probabilities comprises:
identifying each isotopologue by a peak with a specific mass to charge ratio (m/z ratio) position in a 1D mass spectrum;
calculating, for each characterized isotopologue peak, within a specified accuracy tolerance, using the cache data structurem, a set of possible, isotopically-resolved molecular formulas (IMFs) to build the specific IMF(s);

filtering the set of possible IMF(s) against:
i) the NAP
ii) a statistical measure of how well the molecular formula matches the m/z ratio (m/z matching probability), and
iii) metabolite bonding pattern rules.

7. The method of claim 1, wherein identifying a metabolite and its corresponding EMF from statistically-significant cliques of isotopologues with compatible IMFs comprises:
identifying a nonempty intersection between sets of possible EMFs identify from possible IMFs;
statistically evaluating using both the m/z matching probabilities calculated, for each complementary pair of isotopologues from one of the specific respective EMF cliques and statistically comparing a log ratio of isotopologue intensities to a log ratio of each of the IMF NAP,
wherein the isotopologue intensities used in the ratios are derived from associated
characterized peaks; and
identifying specific EMF cliques identified by statically evaluating the sum of complementary pair probabilities/likelihoods against a statistical alpha.

8. The method of claim 7, wherein complementary pair of isotopologues represents a statistically evaluated piece of evidence supporting the existence of the associate EMF clique in the mass spectrum.

9. The system of claim 1, wherein identifying a metabolite and its corresponding EMF from statistically-significant cliques of isotopologues with compatible IMFs comprises:
identifying a nonempty intersection between sets of possible EMFs identify from possible IMFs;
statistically evaluating using both the m/z matching probabilities calculated, for each complementary pair of isotopologues from one of the specific respective EMF cliques and statistically comparing a log ratio of isotopologue intensities to a log ratio of each of the IMF NAP,
wherein the isotopologue intensities used in the ratios are derived from associated
characterized peaks; and
identifying specific EMF cliques identified by statically evaluating the sum of complementary pair probabilities/likelihoods.

10. The method of claim 1, wherein the unknown compound is a metabolite.

11. A system of mass spectrometry data analysis for identification of a specific elemental molecular formula (EMF) for an unknown compound, the system comprising:
computer memory adapted to store mass spectrometry data for an unknown compound; and
a computer processor adapted for performing analytics on mass spectrometry data from mass spectrometry for the unknown compound, said processor:
calculating a natural abundance probability (NAP) of a given isotopologue for isotopes of a predetermined mass and elemental boundary for non-labeling elements of an unknown compound based on chemical norms for possible structures;
creating caches of non-ionized molecular fragments for a subset of isotopes identified using the NAP values for isotopologues above a NAP cutoff which is based on an expected detection dynamic range for a specific mass spectrometry instruction;
sorting the caches of molecular fragments into a requisite cache data structure, to be searched;
characterizing peaks from a raw mass spectrum composed of multiple scans without spectral nor regional averaging for an unknown compound and separating sample-specific peaks from various spectral artefacts seen in ultra-high resolution Fourier transform mass spectra;

creating sets of possible isotope-resolved molecular formulae (IMF) by iteratively searching the molecular fragment caches and combining with additional isotopes and then statistically filtering the results based on NAP and mass-to-charge (m/z) matching probabilities; and identifying an unknown compound and its corresponding EMF from statistically-significant cliques of isotopologues with compatible IMFs.

12. The system of claim 1, wherein calculating a natural abundance probability (NAP) of a given isotopologue for isotopes of non-labeling elements of an unknown compound comprises applying the equation:

$$P_E(k_1, k_2, \ldots, k_m) = \binom{E_{Max}}{k_1, k_2, \ldots, k_m} \prod_{x=1}^{m} NA_{E_{Ix}}^{k_x}$$

$$NAP = \prod_{j=1}^{n} P_{Ej}$$

where, in an instance a specific isotope(s) comes from a labeling source, probability ($P_E$) is omitted from the calculation.

13. The system of claim 11, wherein creating caches of non-ionized molecular fragments for a subset of isotopes identified using the NAP, and sorting the caches of molecular fragments into the requisite cache data structure, comprises enumerating molecular fragments for a given set of isotopes within a mass specified mass range, calculating partial NAP for each molecular fragments, filtering molecular fragments based on a given NAP cutoff, sorting molecular fragments by mass, and generating a binary or b-tree searchable molecular fragment cache.

14. The system of claim 11, wherein characterizing peaks from the raw mass spectrum and separating sample-specific peaks from various spectral artefacts seen in ultra-high resolution Fourier transform mass spectra comprises:

removing noise peaks from multiple mass scans of the unknown compound, corresponding peaks across the multiple scans after noise peaks removed, and performing normalization of peak heights/areas across scans.

15. The system of claim 11, wherein creating sets of possible isotope-resolved molecular formulae (IMF) by iteratively searching the molecular fragment caches and combining with additional isotopes and then statistically filtering the results based on NAP and mass-to-charge (m/z) matching probabilities comprises:

identifying each isotopologue by a peak with a specific mass to charge ratio (m/z ratio) position in a 1D mass spectrum;

calculating, for each characterized isotopologue peak, within a specified accuracy tolerance, using the cache data structurem, a set of possible isotopically-resolved molecular formulas (IMFs) to build the specific IMF(s);

filtering the set of possible IMF(s) against:

i) the NAP ii) a statistical measure of how well the molecular formula matches the m/z ratio (m/z matching probability), and iii) metabolite bonding pattern rules.

16. The system of claim 11, wherein the caches of molecular fragments are stored in the computer memory and/or secondary storage, and said caches in the computer memory and/or the secondary storage are in an order up to multiterabytes in size.

17. The system of claim 11, wherein the unknown compound is a metabolite.

* * * * *